(12) United States Patent
Sato et al.

(10) Patent No.: US 10,537,301 B2
(45) Date of Patent: Jan. 21, 2020

(54) ULTRASOUND DIAGNOSIS APPARATUS, IMAGE PROCESSING APPARATUS, AND IMAGE PROCESSING METHOD

(71) Applicant: Canon Medical Systems Corporation, Otawara-shi (JP)

(72) Inventors: Takeshi Sato, Nasushiobara (JP); Hiroki Takahashi, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 150 days.

(21) Appl. No.: 15/883,813

(22) Filed: Jan. 30, 2018

(65) Prior Publication Data

US 2018/0214116 A1 Aug. 2, 2018

(30) Foreign Application Priority Data

Jan. 31, 2017 (JP) ................................. 2017-015648
Dec. 28, 2017 (JP) ................................. 2017-253370

(51) Int. Cl.
*A61B 8/06* (2006.01)
*A61B 8/08* (2006.01)
(Continued)

(52) U.S. Cl.
CPC .............. *A61B 8/06* (2013.01); *A61B 8/5207* (2013.01); *G06T 7/246* (2017.01); *A61B 8/4488* (2013.01);
(Continued)

(58) Field of Classification Search
USPC ....................................................... 382/128
See application file for complete search history.

(56) References Cited

U.S. PATENT DOCUMENTS 6,245,017 B1 * 6/2001 Hashimoto .............. A61B 8/06
128/916
6,350,238 B1 2/2002 Olstad et al.
(Continued)

FOREIGN PATENT DOCUMENTS

| JP | 3724846 | 12/2005 |
|---|---|---|
| JP | 2014-42823 | 3/2014 |
| JP | 2014-158698 | 9/2014 |

OTHER PUBLICATIONS

Jeremy Bercoff et al. "Ultrafast Compound Doppler Imaging: Providing Full Blood Flow Characterization," IEEE Transactions on Ultrasonics, Ferroelectrics, and Frequency Control, vol. 58, No. 1, Jan. 2011, pp. 14.

(Continued)

*Primary Examiner* — Ishrat I Sherali
(74) *Attorney, Agent, or Firm* — Oblon, McClelland, Maier & Neustadt, L.L.P.

(57) ABSTRACT

An ultrasound diagnosis apparatus includes: transmission and reception circuitry that generates reception signals corresponding to channels, from reflected waves arranged to be received at mutually the same time by transducer elements that transmitted an ultrasound wave, by controlling transducer elements included in an ultrasound probe; extracting circuitry that extracts, prior to a beam forming process, first signals corresponding to the channels from the reception signals corresponding to the channels while suppressing signals originating from a tissue and further extracts a second signal by performing the beam forming process after suppressing, of the extracted first signals corresponding to the channels, a component in a predetermined direction; calculating circuitry that calculates blood flow information from the second signal; and controlling circuitry that generates a blood flow image from the blood flow information and causes display to display the generated blood flow image.

22 Claims, 20 Drawing Sheets

(51) Int. Cl.
    *G06T 7/246*    (2017.01)
    *A61B 8/00*     (2006.01)
(52) U.S. Cl.
    CPC ............. *A61B 8/463* (2013.01); *A61B 8/483* (2013.01); *A61B 8/488* (2013.01); *A61B 8/5223* (2013.01); *A61B 8/5269* (2013.01); *G06T 2207/10132* (2013.01); *G06T 2207/20056* (2013.01); *G06T 2207/30048* (2013.01); *G06T 2207/30104* (2013.01)

(56) References Cited

U.S. PATENT DOCUMENTS

| | | | |
|---|---|---|---|
| 6,685,641 B2 | 2/2004 | Liu | |
| 9,370,338 B2 * | 6/2016 | Hashiba | A61B 8/08 |
| 2010/0331684 A1 * | 12/2010 | Ragauskas | A61B 5/031 600/438 |
| 2013/0144172 A1 * | 6/2013 | Hashiba | A61B 8/08 600/458 |
| 2014/0039317 A1 | 2/2014 | Sato | |
| 2015/0320395 A1 | 11/2015 | Sato | |

OTHER PUBLICATIONS

Hiroki Takahashi et al. "Echo motion imaging with adaptive clutter filter for assessment of cardiac blood flow," Japanese Journal of Applied Physics 54, http://dx.doi.org/10.7567/JJAP.54.07HF09, 2015, pp. 9.
Damien Garcia et al. "Stolt's f-k migration for plane wave ultrasound imaging," IEEE Trans Ultrason Ferroelectr Freq Control. Author manuscript; available in PMC 2014, 10.1109/TUFFC.2013.2771, Sep. 2013, pp. 28.

* cited by examiner

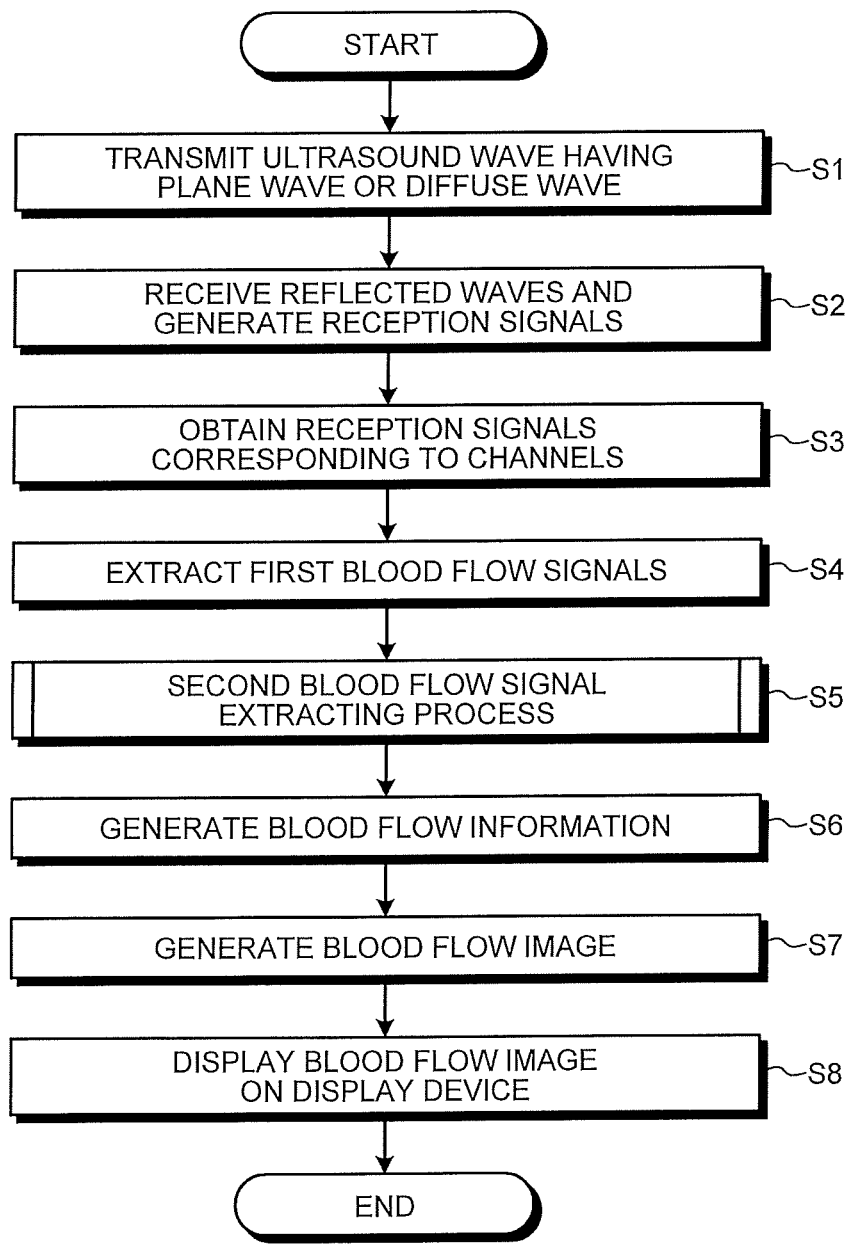

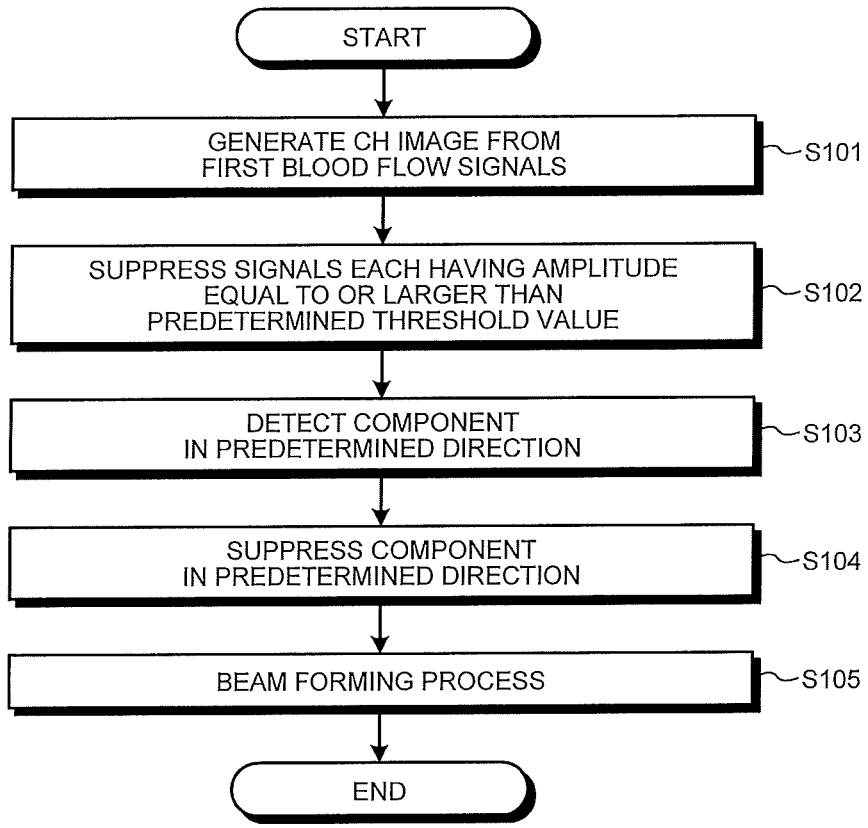
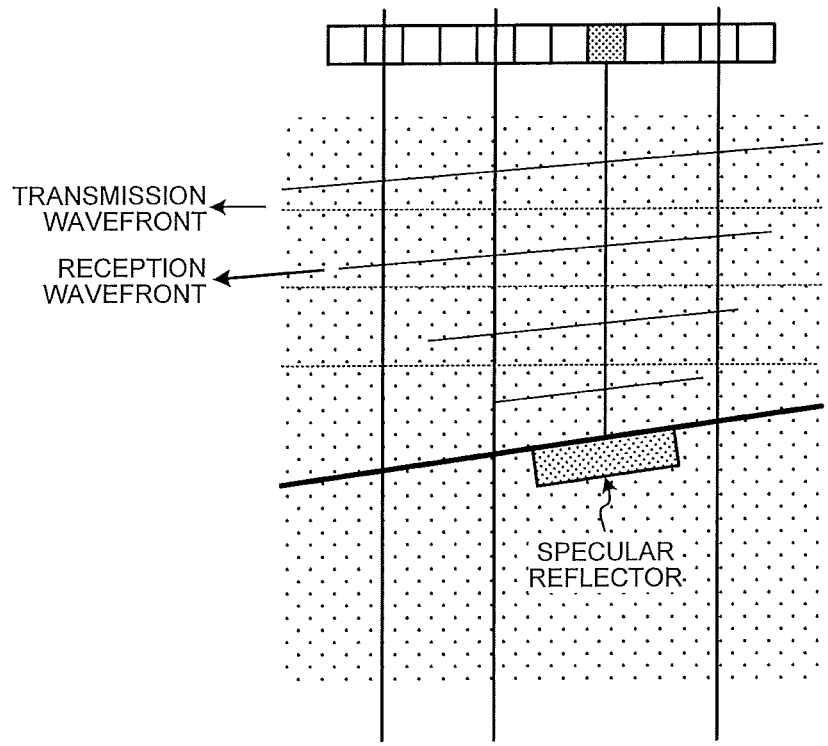

ULTRASOUND DIAGNOSIS APPARATUS, IMAGE PROCESSING APPARATUS, AND IMAGE PROCESSING METHOD

CROSS-REFERENCE TO RELATED APPLICATIONS

This application is based upon and claims the benefit of priority from Japanese Patent Application No. 2017-015648, filed on Jan. 31, 2017 and Japanese Patent Application No. 2017-253370, filed on Dec. 28, 2017; the entire contents of which are incorporated herein by reference.

FIELD

Embodiments described herein relate generally to an ultrasound diagnosis apparatus, an image processing apparatus, and an image processing method.

BACKGROUND

In recent years, it is possible to perform an ultrasound scan (called "an all-raster parallel simultaneous reception") where either a plane wave or a diffuse wave is transmitted, and reflected-wave signals are received in a real-time manner by all the reception raster elements within an ultrasound frame with respect to the transmission at a time. Further, a blood flow display system (called "an ultrahigh-speed framerate method") is known in which the all-raster parallel simultaneous reception is applied to a blood flow imaging method (called "a high framerate method") utilizing an ultrasound scan (called "a high framerate ultrasound scan") in which data sequences between frames are used as Doppler data sequences.

According to the ultrahigh-speed framerate method, for example, when the transmission interval of the ultrasound waves at a time is 200 μs, the framerate can be calculated as 5,000 frames per second (fps). Further, Moving Target Indicator (MTI) filters are capable of processing frame data corresponding to any number of frames. In other words, because the ultrahigh-speed framerate method is capable of arranging the transmission interval of the ultrasound waves to match the framerate, it is possible to obtain an infinite time period for observation while ensuring display at a high framerate and a high folding velocity. In other words, by implementing the ultrahigh-speed framerate method, it is possible to structure a steep MTI filter having a low cut-off frequency. With these arrangements, according to the ultrahigh-speed framerate method, by eliminating as many clutters as possible, it is possible to detect blood flows in a wide range from blood flows having lower flow rates to blood flows having higher flow rates.

Further, as an adaptive example of the ultrahigh-speed framerate method, observing moving images at 5,000 fps in a slow playback mode makes it possible to visually recognize complex flows of blood flowing through the heart, the carotid artery, or the like. Furthermore, tracking a speckle in a blood flow makes it possible to display a flow of blood with a two-dimensional vector.

BRIEF DESCRIPTION OF THE DRAWINGS

FIG. 14 is a flowchart illustrating a procedure in a process performed by the ultrasound diagnosis apparatus according to the first embodiment;

FIG. 15 is a flowchart illustrating a procedure in a second blood flow signal extracting process performed by the Doppler processing circuitry according to the first embodiment;

FIG. 16 is a drawing for explaining a modification example of the first embodiment;

DETAILED DESCRIPTION

An ultrasound diagnosis apparatus includes transmission and reception circuitry, extracting circuitry, calculating circuitry, and controlling circuitry. The transmission and reception circuitry generates reception signals corresponding to a plurality of channels, from reflected waves arranged to be received at a mutually same time by a plurality of transducer elements that transmitted an ultrasound wave, by controlling multiple transducer elements included in an ultrasound probe. The extracting circuitry extracts, prior to a beam forming process, first signals corresponding to the plurality of channels from the reception signals corresponding to the channels while suppressing signals originating from a tissue and to further extract a second signal by performing the beam forming process after suppressing, of the extracted first signals corresponding to the plurality of channels, a component in a predetermined direction. The calculating circuitry calculates blood flow information from the second signal. The controlling circuitry generates a blood flow image from the blood flow information and to cause a display to display the generated blood flow image.

Exemplary embodiments of an ultrasound diagnosis apparatus, an image processing apparatus, and an image processing method will be explained below, with reference to the accompanying drawings. Possible embodiments are not limited to the embodiments described below. Further, the contents of any of the embodiments are, in principle, similarly applicable to any other embodiment.

First Embodiment

Figure 1:
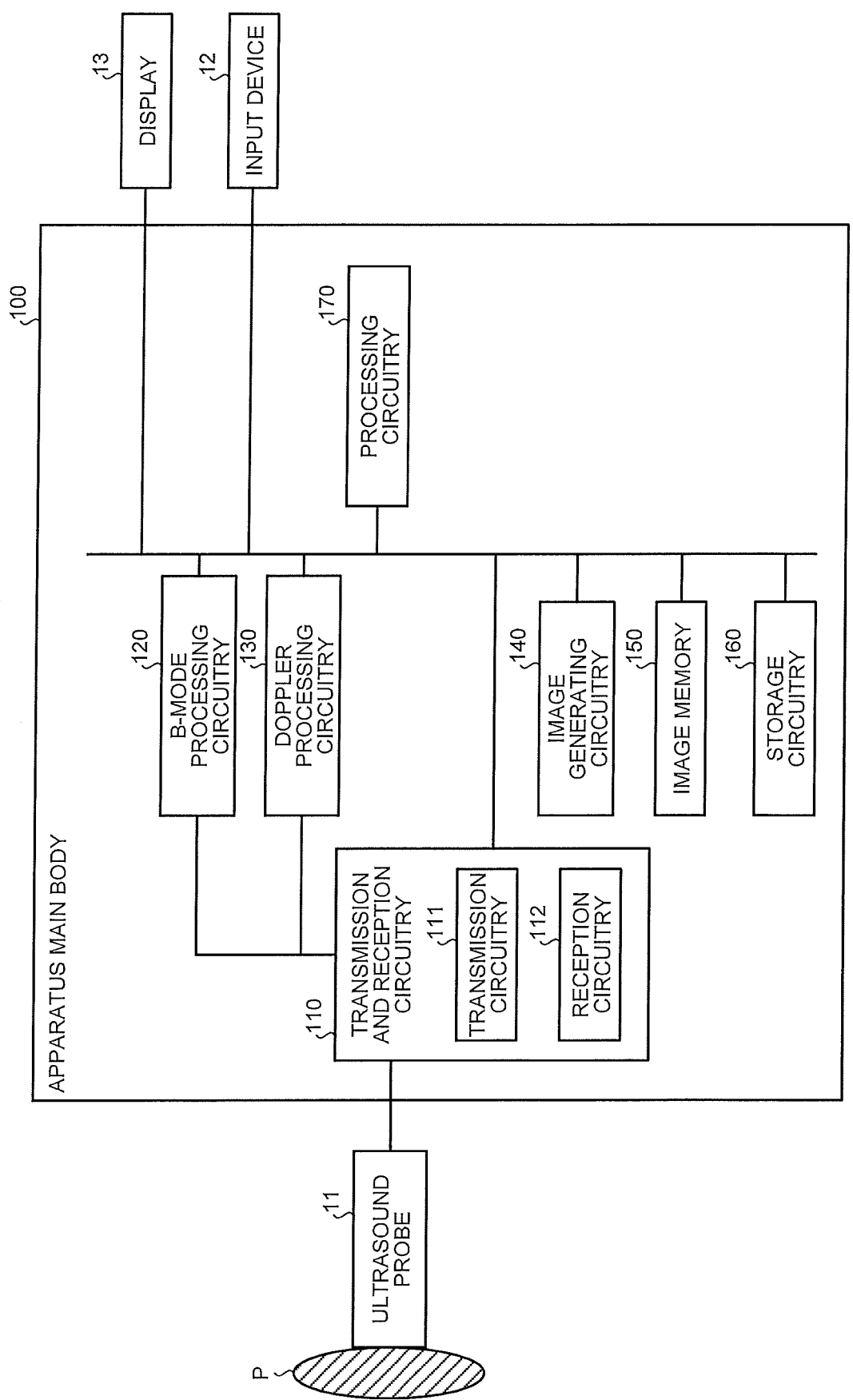
FIG. 1 is a block diagram illustrating an exemplary configuration of an ultrasound diagnosis apparatus according to a first embodiment.

FIG. 1 is a block diagram illustrating an exemplary configuration of an ultrasound diagnosis apparatus 1 according to a first embodiment. As illustrated in FIG. 1, the ultrasound diagnosis apparatus 1 according to the first embodiment includes an ultrasound probe 11, an input device 12, a display 13, and an apparatus main body 100. The ultrasound probe 11 is connected to transmission and reception circuitry 110 (explained later) included in the apparatus main body 100 so as to be able to communicate therewith. Further, the input device 12 and the display 13 are connected to various types of circuits included in the apparatus main body 100 so as to be able to communicate therewith.

The ultrasound probe 11 is brought into contact with the body surface of an examined subject (hereinafter, "patient") P and is configured to transmit and receive an ultrasound wave. For example, the ultrasound probe 11 includes a plurality of piezoelectric transducer elements (which may simply be referred to as "transducer elements"). The plurality of piezoelectric transducer elements are configured to generate an ultrasound wave on the basis of a transmission signal supplied thereto from the transmission and reception circuitry 110. The generated ultrasound wave is reflected on tissues in the body of the patient P and is received by the plurality of piezoelectric transducer elements as reflected-wave signals. The ultrasound probe 11 sends the reflected-wave signals received by the plurality of piezoelectric transducer elements, to the transmission and reception circuitry 110. In this manner, the ultrasound probe 11 transmits the ultrasound wave and receives reflected waves.

In the first embodiment, the ultrasound probe 11 may be a one-dimensional (1D) array probe configured to scan a two-dimensional region (perform a two-dimensional scan) inside the patient P or may be a mechanical four-dimensional (4D) probe or a two-dimensional (2D) array probe configured to scan a three-dimensional region (perform a three-dimensional scan) inside the patient P. Alternatively, the ultrasound probe 11 may be a linear probe, a convex probe, or a sector probe.

The input device 12 corresponds to, for example, a mouse, a keyboard, a button, a panel switch, a touch command screen, a foot switch, a trackball, a joystick, and/or the like. The input device 12 is configured to receive various types of setting requests from an operator of the ultrasound diagnosis apparatus 1 and to transfer the received various types of setting requests to any of the circuits included in the apparatus main body 100, as appropriate.

The display 13 is configured to display a Graphical User Interface (GUI) used by the operator to input the various types of setting requests through the input device 12 and to display an image (an ultrasound image) based on ultrasound image data generated by the apparatus main body 100 or the like.

The apparatus main body 100 is an apparatus configured to generate the ultrasound image data on the basis of the reflected-wave signals received by the ultrasound probe 11. As illustrated in FIG. 1, the apparatus main body 100 includes, for example, the transmission and reception circuitry 110, B-mode processing circuitry 120, Doppler processing circuitry 130, image generating circuitry 140, an image memory 150, storage circuitry 160, and processing circuitry 170. The transmission and reception circuitry 110, the B-mode processing circuitry 120, the Doppler processing circuitry 130, the image generating circuitry 140, the image memory 150, the storage circuitry 160, and the processing circuitry 170 are connected together so as to be able to communicate with one another.

The transmission and reception circuitry 110 is configured to control the transmission and the reception of the ultrasound wave performed by the ultrasound probe 11. For example, the transmission and reception circuitry 110 includes transmission circuitry 111 and reception circuitry 112 and is configured to control the transmission and the reception of the ultrasound wave performed by the ultrasound probe 11, on the basis of an instruction from the processing circuitry 170 (explained later).

The transmission circuitry 111 is configured to generate transmission waveform data and to further generate the transmission signal to be used by the ultrasound probe 11 for transmitting the ultrasound wave, from the generated transmission waveform data. After that, by applying the transmission signal to the ultrasound probe 11, the transmission circuitry 111 is configured to cause an ultrasound beam to be transmitted in which the ultrasound wave is converged in the form of a beam.

The reception circuitry 112 is configured to generate the reflected-wave data in which reflected components from directions corresponding to reception directionalities of the reflected-wave signals are emphasized, by performing an adding process by applying a predetermined delay time period to the reflected-wave signals received by the ultrasound probe 11 and is configured to transmit the generated reflected-wave data to the B-mode processing circuitry 120 and the Doppler processing circuitry 130.

For example, the reception circuitry 112 includes an amplifying circuit (hereinafter "Amp", as necessary), an Analog/Digital (A/D) converter (hereinafter "ADC", as necessary), a quadrature detecting circuit (hereinafter "IQ", as necessary), and the like. The amplifying circuit is configured to amplify the reflected-wave signal for each of the channels and to perform a gain correcting process thereon. The A/D converter is configured to perform an A/D conversion on the reflected-wave signals resulting from the gain correcting process.

Further, the quadrature detecting circuit is configured to convert the reflected-wave signals resulting from the A/D conversion into an In-phase signal (an I signal) and a Quadrature-phase signal (a Q signal) that are in a baseband. Further, the quadrature detecting circuit is configured to store the I signal and the Q signal (hereinafter, "IQ signals") into a buffer as the reflected-wave data.

In the transmission and reception circuitry 110 configured as described above, the transmission circuitry 111 is configured to control the plurality of transducer elements included in the ultrasound probe 11 so as to transmit either an ultrasound wave having a plane wave or an ultrasound wave having a diffuse wave (an ultrasound wave spreading over a wide range similarly to that in the transmission of the ultrasound wave having a plane wave). For example, under control of the processing circuitry 170, the transmission circuitry 111 may cause the ultrasound probe 11 to transmit the ultrasound wave having the plane wave or may cause the ultrasound probe 11 to transmit the ultrasound wave having the diffuse wave.

In this situation, for example, when a plane wave transmission is performed during a linear scan that uses a linear probe as the ultrasound probe 11, the transmission circuitry 111 causes an ultrasound wave to be transmitted mutually at the same time by a plurality of transducer elements within an opening. As another example, when a diffuse wave transmission is performed during a convex scan that uses a convex probe as the ultrasound probe 11, the transmission circuitry 111 also similarly causes an ultrasound wave to be transmitted mutually at the same time by a plurality of transducer elements within an opening. As yet another example, when a diffuse wave transmission is performed during a sector scan that uses a sector probe as the ultrasound probe 11, the transmission circuitry 111 causes an ultrasound wave having a diffuse wave to be transmitted by exercising transmission delay control.

Figure 2:
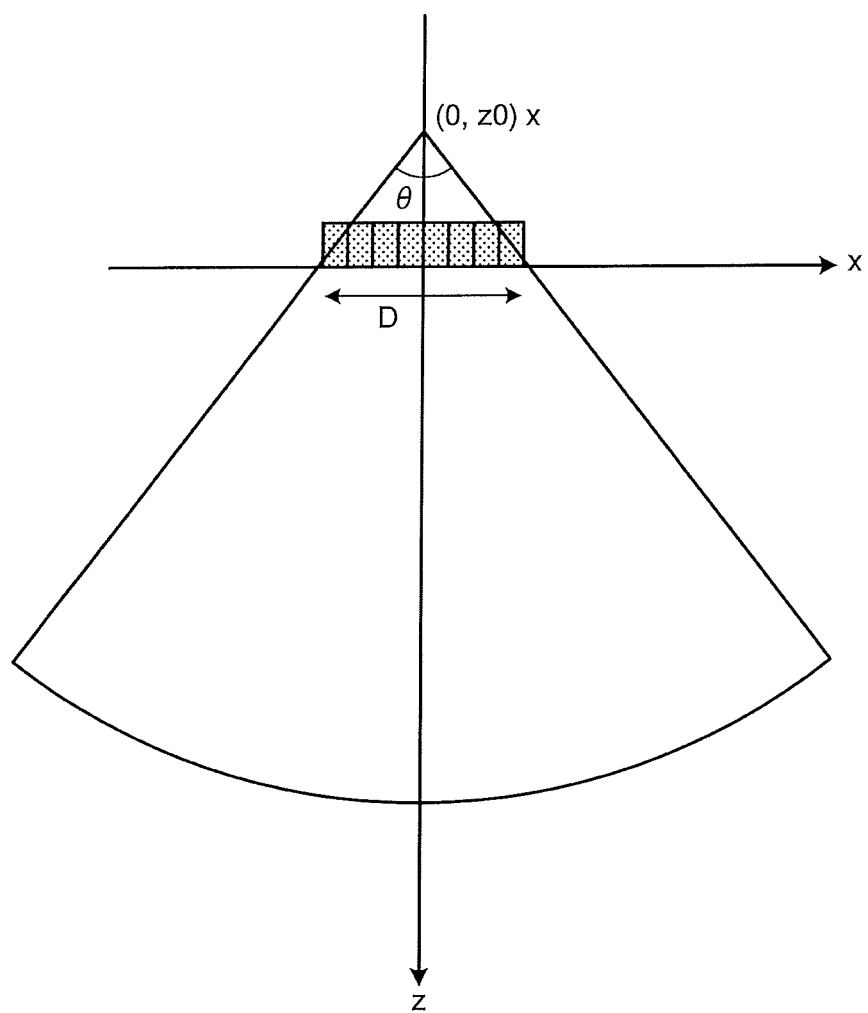
FIG. 2 is a chart for explaining transmission delay control that is exercised when a diffuse wave transmission is performed during a sector scan using a sector probe.

FIG. 2 is a chart for explaining the transmission delay control that is exercised when a diffuse wave transmission is performed during a sector scan using a sector probe. FIG. 2 illustrates eight transducer elements on the x-axis. As illustrated in FIG. 2, the transmission circuitry 111 performs the diffuse wave transmission by setting a virtual transmission focus position (0,z0) behind the transducer elements and exercising transmission delay control as if the wavefront was propagating from behind the transducer elements. The example in FIG. 2 illustrates a situation in which the transmission circuitry 111 causes an ultrasound wave having a diffuse wave to be transmitted from the eight transducer elements in the opening width D, by exercising the transmission delay control so that the ultrasound wave concentrically diffuses from the virtual transmission focus position (0,z0) in the range having the angle θ.

Further, the reception circuitry 112 causes the ultrasound probe 11 to perform an ultrasound scan in which the plurality of transducer elements that transmitted the ultrasound wave receive reflected-wave signals at the same time as one another. Further, the reception circuitry 112 generates reception signals corresponding to a plurality of channels from the reflected-wave signals arranged to be received mutually at the same time by the plurality of transducer elements that transmitted the ultrasound wave. In the following sections, an ultrasound scan realized by causing the transmission circuitry 111 to transmit either an ultrasound wave having a plane wave or an ultrasound wave having a diffuse wave and further causing the reception circuitry 112 to have the reflected-wave signals received mutually at the same time by the plurality of transducer elements that transmitted the ultrasound wave will be referred to as an "all-raster parallel simultaneous reception". When performing the all-raster parallel simultaneous reception, all the plurality of transducer elements included in the ultrasound probe 11 do not necessarily have to be used simultaneously. For example, it is acceptable to divide the plurality of transducer elements included in the ultrasound probe 11 into blocks, so as to perform an ultrasound scan implementing the all-raster parallel simultaneous reception, by using the transducer elements in units of blocks.

Further, under the control of the processing circuitry 170, the transmission circuitry 111 causes the ultrasound probe 11 to perform an ultrasound scan (hereinafter, "a high framerate ultrasound scan") that uses data sequences between frames as Doppler data sequences (see Japanese Granted Patent No. 3724846 and Japanese Patent Application Laid-open No. 2014-42823). For example, under the control of the processing circuitry 170, the transmission circuitry 111 causes the ultrasound probe 11 to perform a first ultrasound scan to obtain information about movements of a moving member within a first scan range and causes the ultrasound probe 11 to perform a second ultrasound scan to obtain information about the shapes of tissues within a second scan range, by performing an ultrasound scan corresponding to each of a plurality of divided ranges obtained by dividing the second scan range, during the first ultrasound scan in a time-division manner. A blood flow imaging method that uses the high framerate ultrasound scan will be referred to as a "high framerate method".

The B-mode processing circuitry 120 is configured to perform various types of signal processing processes on the reflected-wave data generated by the reception circuitry 112 from the reflected-wave signals. The B-mode processing circuitry 120 generates data (B-mode data) in which signal intensities corresponding to sampling points (measuring points) are expressed by degrees of brightness, by performing a logarithmic amplification, an envelope detection, and/or the like on the reflected-wave data received from the reception circuitry 112. The B-mode processing circuitry 120 sends the generated B-mode data to the image generating circuitry 140.

Further, the B-mode processing circuitry 120 is configured to perform a signal processing process for the purpose of performing a harmonic imaging process to render harmonic components in a picture. Known examples of the harmonic imaging process include a Contrast Harmonic Imaging (CHI) process and a Tissue Harmonic Imaging (THI) process. Further, examples of scanning schemes that can be used during a contrast harmonic imaging process or a tissue harmonic imaging process include: an Amplitude Modulation (AM) scheme; a Phase Modulation (PM) scheme which may be called a "pulse subtraction method" or a "pulse inversion method"; and an AMPM scheme with which it is possible to achieve advantageous effects of both the AM scheme and the PM scheme, by using the AM scheme and the PM scheme in combination.

The Doppler processing circuitry 130 is configured to generate data (Doppler data) obtained by extracting movement information of moving members based on a Doppler effect, from the reflected-wave data received from the reception circuitry 112 at multiple sampling points in a scanned region. More specifically, as the movement information of the moving members, the Doppler processing circuitry 130 generates Doppler data obtained by extracting an average velocity value, a dispersion value, a power value, and/or the like at the multiple sampling points. In this situation, the moving members may be, for example, blood flows, tissues such as the cardiac wall, and a contrast agent. The Doppler processing circuitry 130 sends the generated Doppler data to the image generating circuitry 140.

The image generating circuitry 140 is configured to generate the ultrasound image data from the data generated by the B-mode processing circuitry 120 and the Doppler processing circuitry 130. For example, the image generating circuitry 140 is configured to generate B-mode image data in which intensities of the reflected waves are expressed by degrees of brightness, from the B-mode data generated by the B-mode processing circuitry 120. Further, the image generating circuitry 140 is configured to generate Doppler image data expressing moving member information (blood flow information), from the Doppler data generated by the Doppler processing circuitry 130. The Doppler image data may be velocity image data, dispersion image data, power image data, or image data combining any of these. In other words, the image generating circuitry 140 is configured to generate a blood flow image from the blood flow information.

The image memory 150 is a memory configured to store therein data generated by the B-mode processing circuitry 120, the Doppler processing circuitry 130, and the image generating circuitry 140. For example, the image memory 150 stores therein the ultrasound image data generated by the image generating circuitry 140 so as to be kept in correspondence with an electrocardiographic waveform of the patient P.

The storage circuitry 160 is a storage device configured to store therein various types of data. For example, the storage circuitry 160 is configured to store therein control computer programs used for performing ultrasound transmission and reception processes, image processing processes, and display processes, as well as diagnosis information (e.g., patients' IDs, observations of medical doctors) and various types of data such as diagnosis protocols and various types of body marks. Further, it is possible to transfer any of the data stored in the storage circuitry 160 to an external apparatus via an interface unit (not illustrated).

Further, the storage circuitry 160 is configured to store therein data generated by the B-mode processing circuitry 120, the Doppler processing circuitry 130, and the image generating circuitry 140. For example, the storage circuitry 160 is configured to store therein ultrasound image data corresponding to a predetermined number of heartbeats designated by the operator.

The processing circuitry 170 is configured to control the overall processes performed by the ultrasound diagnosis apparatus 1. More specifically, on the basis of the various types of setting requests input by the operator via the input device 12 as well as the various types of control computer programs and various types of data read from the storage circuitry 160, the processing circuitry 170 is configured to control processes performed by the transmission and reception circuitry 110, the B-mode processing circuitry 120, the Doppler processing circuitry 130, the image generating circuitry 140, and the like. Further, the processing circuitry 170 is configured to cause the display 13 to display any of the ultrasound image data stored in the image memory 150. For example, the processing circuitry 170 causes the display 13 to display the B-mode image data stored in the image memory 150. As another example, the processing circuitry 170 causes the display 13 to display the Doppler image data stored in the image memory 150.

For example, the processing circuitry 170 controls the transmission circuitry 111 and the reception circuitry 112 so as to cause the ultrasound probe 11 to perform the all-raster parallel simultaneous reception. In other words, the processing circuitry 170 causes the transmission circuitry 111 to transmit either an ultrasound wave having a plane wave or an ultrasound wave having a diffuse wave, and also causes the reception circuitry 112 to have the reflected-wave signals received mutually at the same time by the plurality of transducer elements that transmitted the ultrasound wave. Further, for example, the processing circuitry 170 controls the transmission circuitry 111 so as to cause the ultrasound probe 11 to perform a high framerate ultrasound scan. In other words, the processing circuitry 170 causes the ultrasound probe 11 to perform the first ultrasound scan to obtain information about movements of moving members within the first scan range and causes the ultrasound probe 11 to perform the second ultrasound scan to obtain information about the shapes of tissues within the second scan range, by performing an ultrasound scan corresponding to each of a plurality of divided ranges obtained by dividing the second scan range, during the first ultrasound scan in a time-division manner. Further, for example, the processing circuitry 170 controls the transmission circuitry 111 and the reception circuitry 112 so as to cause the ultrasound probe 11 to implement the ultrahigh-speed framerate method realized by applying the all-raster parallel simultaneous reception to the high framerate method.

It is also acceptable to integrate two or more of the constituent elements illustrated in FIG. 1 into a single processor so as to realize the functions thereof. The term "processor" used in the above explanation denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions thereof by reading and executing computer programs (hereinafter, "programs") stored in the storage circuitry 160. Alternatively, it is also acceptable to have the programs directly incorporated into the circuits of the processors, instead of storing the programs in the storage circuitry 160. In that situation, the processors realize the functions by reading and executing the programs incorporated in the circuits thereof. Each of the processors according to the present embodiment does not necessarily have to be individually configured as a single circuit. Alternatively, one processor may be structured by combining together a plurality of independent circuits, so as to realize the functions thereof.

In the ultrasound diagnosis apparatus 1 configured as described above, a method (a color Doppler method) by which a blood flow is rendered in a picture by using an ultrasound wave is widely and popularly used. In this situation, a B-mode image displays signals in a dynamic range as large as 60 dB; however, a blood flow image displays signals in a small range such as approximately 20 dB. For this reason, for example, when an ultrasound scan (the all-raster parallel simultaneous reception) is performed by performing either a plane wave transmission or a diffuse wave transmission and, with respect to the transmission at a time, the reflected-wave signals are received in a real-time manner by all the reception raster elements within an ultrasound frame, the B-mode images clearly exhibits degradation of resolution in the orientation direction, whereas the blood flow image does not exhibit so much degradation of resolution in the orientation direction.

As explained above, because blood flow images do not have a significant problem of degradation of resolution in the orientation direction, there is a possibility that displaying a blood flow by performing a plane wave transmission or a diffuse wave transmission may be able to provide clinical images that are useful in many situations. However, when the all-raster parallel simultaneous reception is performed, signals from a specular reflector (a highly-reflective member) such as a valve or a wall of the heart may appear as an artifact in blood flow images, in some situations.

Figure 3:
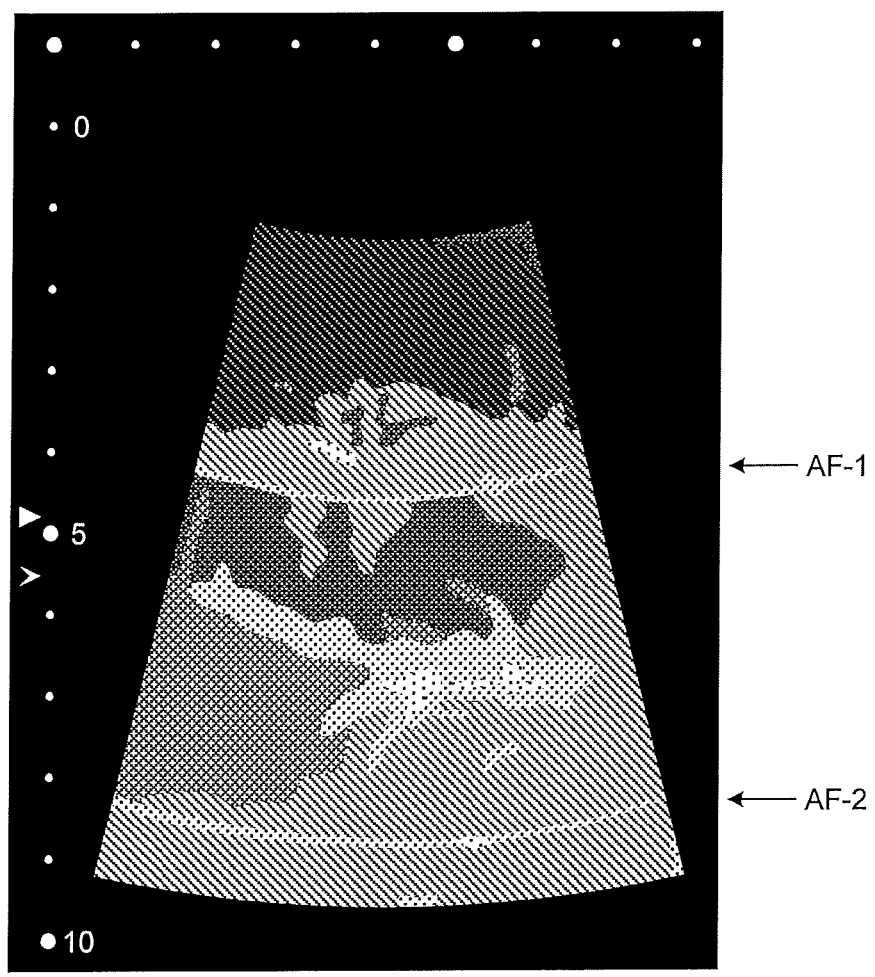
FIG. 3 is a drawing illustrating an example of artifacts caused by a specular reflector.
Figure 4:
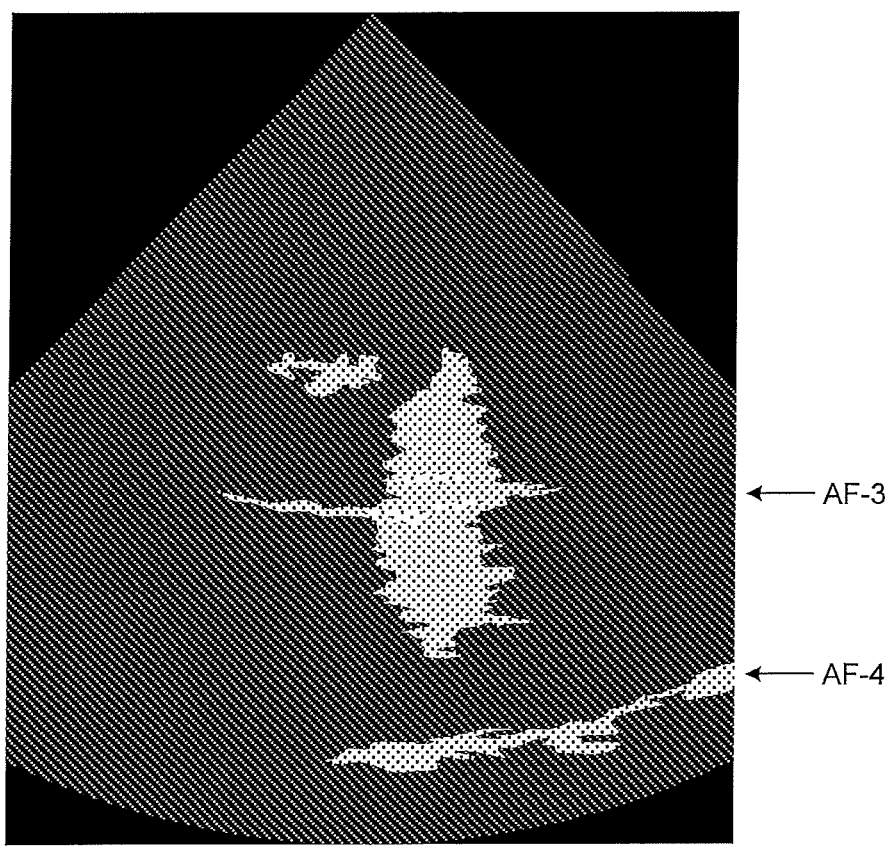
FIG. 4 is a drawing illustrating another example of artifacts caused by the specular reflector.

FIGS. 3 and 4 are drawings illustrating examples of artifacts caused by a specular reflector. FIGS. 3 and 4 illustrate the examples in which the blood flow information is displayed in a power image. FIG. 3 illustrates an example of an image displaying blood flow signals of the liver by performing a diffuse wave transmission while using a convex probe. In FIG. 3, artifacts AF-1 and AF-2 are occurring in the shape of arcs. FIG. 4 illustrates an image displaying blood flow signals of the heart by performing a diffuse wave transmission while using a sector probe. In FIG. 4, artifacts AF-3 and AF-4 are occurring in the shape of arcs, in the same manner as in FIG. 3.

Incidentally, a method has been disclosed by which an attempt is made to reduce such arc-shaped artifacts. For example, according to a first method described in Non Patent Literature 1 (Takahashi et al, Echo motion imaging with adaptive clutter filter for assessment of cardiac blood flow, Japanese Journal of Applied Physics, June 2015, vol. 54, no. 7, pp. 07HF09-1-8), arc-shaped artifacts are reduced by varying the cut-off frequency of an MTI filter in accordance with movements of the heart in the B-mode.

According to the first method, arc-shaped artifacts occur in a temporal phase during which a highly-reflective member such as a valve moves at a high speed. During such a temporal phase, the occurrence of artifacts is suppressed by raising the cut-off frequency of the MTI filter. However, raising the cut-off frequency also means suppressing the blood flow signals. Accordingly, a problem may be caused in observation of flows of blood or calculation of two-dimensional velocity vectors. Further, even when the cut-off frequency of the MTI filter is raised, it is not possible to completely eliminate the arc-shaped artifacts.

According to a second method described in Non Patent Literature 2 (Bercoff et al, Ultrafast Compound Doppler Imaging: Providing Full Blood Flow Characterization, IEEE Transactions on Ultrasonics, Ferroelectrics, and Frequency Control, 2011, Vol. 58, No. 1, pp. 134-147), it is possible to achieve a level of performance that is equal to or higher than that with a normal transmission focus, by transmitting a plane wave from multiple directions and performing an addition in a coherent manner after correcting positions. The second method seems to be a very reasonable method. However, the second method has a problem where the framerate is lowered due to the multiple transmissions. Further, adding reception signals together involves applying a Low Pass Filter (LPF) to Doppler signals. Thus, another problem arises where blood flows having high flow rates may be removed. These two problems should not be overlooked in situations where flows of blood are visually observed and where two-dimensional velocity vectors are to be calculated.

For the purpose of reducing side lobes, adaptive beam forming techniques are known by which a Minimum Variance (MV) method, an Amplitude and Phase Estimation (APES) method, or a Phase Coherence Imaging (PCI) method is implemented. However, when we tried adaptive beam forming processes with the MV method, the APES method, and the PCI method, arc-shaped artifacts were hardly reduced.

In view of these circumstances, it is desirable to be able to eliminate artifacts such as those illustrated in FIGS. 3 and 4, for example, that occur when a blood flow is displayed by performing the all-raster parallel simultaneous reception by transmitting a plane wave or a diffuse wave. In the following sections, a method for addressing side lobes occurring from a highly-reflective member will be explained.

Figure 5:
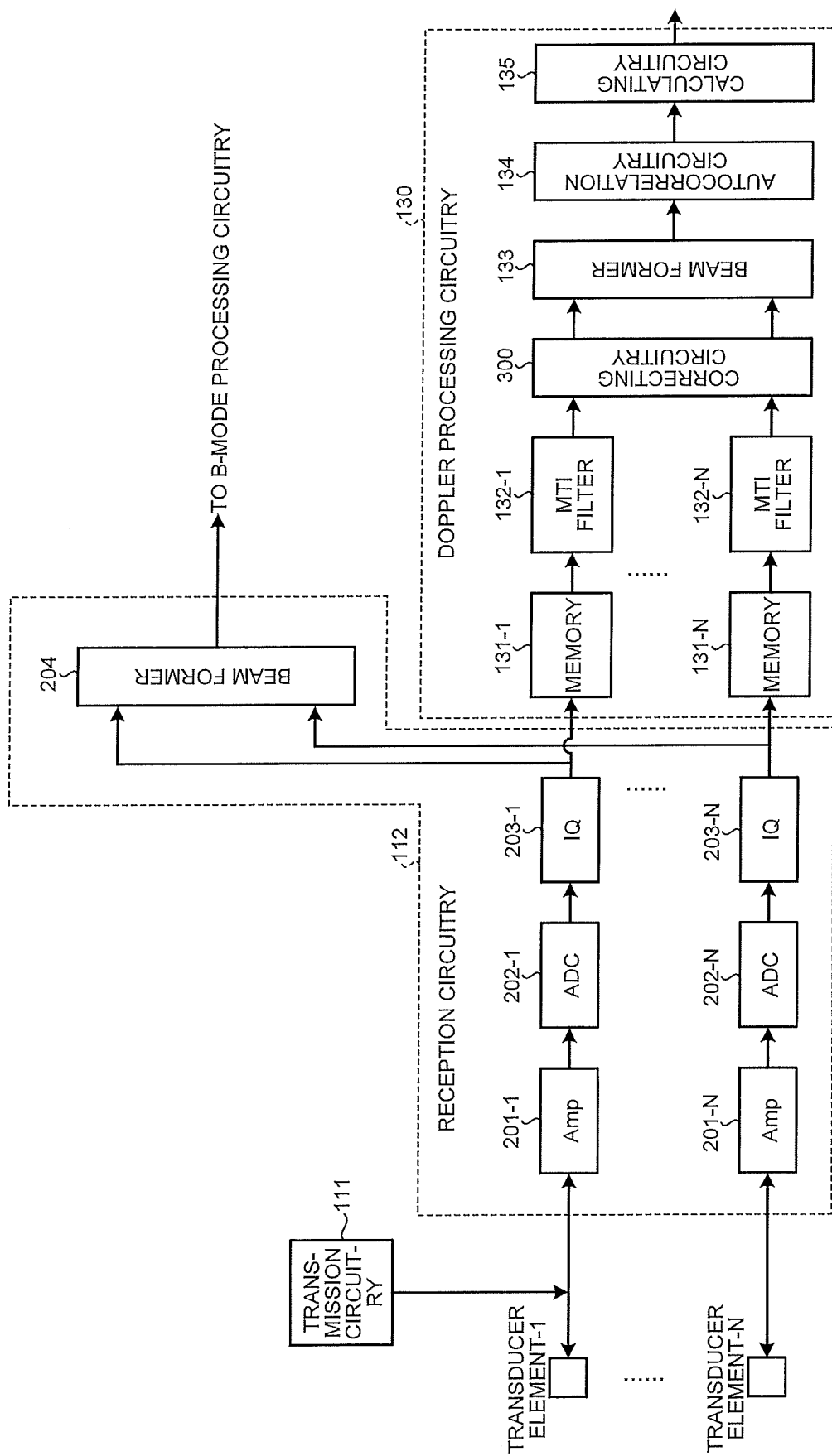
FIG. 5 is a diagram illustrating exemplary configurations of reception circuitry and Doppler processing circuitry according to the first embodiment.

First, exemplary configurations of the reception circuitry 112 and the Doppler processing circuitry 130 according to the first embodiment will be explained, with reference to FIG. 5. FIG. 5 is a diagram illustrating the exemplary configurations of the reception circuitry 112 and the Doppler processing circuitry 130 according to the first embodiment.

The transducer elements generate an ultrasound wave on the basis of the transmission signal supplied thereto from the transmission circuitry 111. The generated ultrasound wave is reflected on tissues in the body of the patient P and is received as the reflected-wave signals by the plurality of piezoelectric transducer elements. The transducer elements send the received reflected-wave signals to the reception circuitry 112. With reference to FIG. 5, an example will be explained in which a blood flow image is displayed by implementing the ultrahigh-speed framerate method realized by applying the all-raster parallel simultaneous reception to the high framerate method.

Under the control of the processing circuitry 170, the transmission circuitry 111 causes the ultrasound probe 11 to perform an ultrasound scan that uses data sequences between frames as Doppler data sequences (see Japanese Granted Patent No. 3724846 and Japanese Patent Application Laid-open No. 2014-42823). After that, the reception circuitry 112 generates reception signals corresponding to each frame, by scanning one frame every time the ultrasound probe 11 is caused to transmit and receive an ultrasound wave.

Further, the transmission circuitry 111 causes the ultrasound wave to be transmitted by controlling a plurality of transducer elements included in the ultrasound probe. For example, the transmission circuitry 111 causes an ultrasound wave having either a plane wave or a diffuse wave to be transmitted, by controlling a plurality of transducer elements included in the ultrasound probe 11. Further, the reception circuitry 112 causes the ultrasound probe 11 to perform an ultrasound scan in which the reflected-wave signals are received mutually at the same time by the plurality of transducer elements that transmitted the ultrasound wave.

As illustrated in FIG. 5, the reception circuitry 112 is connected to transducer elements (a transducer element-1, . . . , and a transducer element-N) of which the quantity is equal to N. The transducer elements correspond to the channels. Further, as illustrated in FIG. 5, as sub circuits to process the reflected-wave signal received by the transducer element-1, the reception circuitry 112 includes an amplifying circuit 201-1 ("Amp" in FIG. 5), an A/D converter 202-1 ("ADC" in FIG. 5), and a quadrature detecting circuit 203-1 ("IQ" in FIG. 5). Similarly, as sub circuits to process the reflected-wave signal received by the transducer element-N, the reception circuitry 112 includes an amplifying circuit 201-N ("Amp" in FIG. 5), an A/D converter 202-N ("ADC" in FIG. 5), and a quadrature detecting circuit 203-N ("IQ" in FIG. 5).

In the present example, when it is not necessary to distinguish the amplifying circuit 201-1 and the amplifying circuit 201-N from each other, these amplifying circuits will be referred to as the amplifying circuits 201. When it is not necessary to distinguish the A/D converter 202-1 and the A/D converter 202-N from each other, these A/D converters will be referred to as the A/D converters 202. When it is not necessary to distinguish the quadrature detecting circuit 203-1 and the quadrature detecting circuit 203-N from each other, these quadrature detecting circuits will be referred to as the quadrature detecting circuits 203. In other words, the reception circuitry 112 is provided with an amplifying circuit 201, an A/D converter 202, and a quadrature detecting circuit 203 for each of the transducer elements (each of the channels). In this situation, as explained above, each of the amplifying circuits 201 amplifies the reflected-wave signal in correspondence with the channel thereof and performs the gain correcting process. Further, each of the A/D converters 202 performs the A/D conversion on the corresponding reflected-wave signal resulting from the gain correcting process. Each of the quadrature detecting circuits 203 converts the corresponding reflected-wave signal into an In-phase signal (an I signal) and a Quadrature-phase signal (a Q signal) that are in a baseband. Further, each of the quadrature detecting circuits 203 sends the I signal and the Q signal resulting from the conversion, to the Doppler processing circuitry 130. Further, each of the quadrature detecting circuits 203 sends the I signal and the Q signal resulting from the conversion, to a beam former 204.

The beam former 204 is configured to execute a beam forming function. In other words, the beam former 204 is configured to generate the reflected-wave data by performing a phasing addition process that uses the I signal and the Q signal corresponding to each of the channels and resulting from the conversion performed by the quadrature detecting circuits 203. The beam former 204 outputs the generated reflected-wave data to the B-mode processing circuitry 120.

As sub circuits to perform processes on the reflected-wave signal received by the transducer element-1, the Doppler processing circuitry 130 includes a memory 131-1 and an MTI filter 132-1. Further, as sub circuits to perform processes on the reflected-wave signal received by the transducer element-N, the Doppler processing circuitry 130 includes a memory 131-N and an MTI filter 132-N. In the present example, when it is not necessary to distinguish the memory 131-1 and the memory 131-N from each other, these memories will be referred to as the memories 131. When it is not necessary to distinguish the MTI filter 132-1 and the MTI filter 132-N from each other, these MTI filters will be referred to as the MTI filters 132. The MTI filters may be referred to as filtering processing circuits. Further, the Doppler processing circuitry 130 includes a beam former 133, autocorrelation circuitry 134, and calculating circuitry 135.

Each of the memories 131 is configured to store therein the reception signals corresponding to a plurality of frames of the corresponding one of the channels. In this situation, it is assumed that each of the memories 131 has a capacity to be able to store the reception signals corresponding to the plurality of frames of the corresponding one of the channels.

Each of the MTI filters 132 is configured to execute an MTI filtering function. Although there are various methods for performing a scan to display blood flows, the high framerate method will be explained in the following sections. More specifically, each of the MTI filters 132 is configured to extract first blood flow signals by applying a filter configured to suppress signals originating from tissues to between frames. For example, images corresponding to a number of frames are stored into the memories 131, the frames each being obtained by performing the all-raster parallel simultaneous reception with respect to the transmission at a time. Further, by performing the filtering process between the frames, the signals originating from the tissue are eliminated. In other words, each of the MTI filters 132 performs the filtering process by using the data sequences between the frames as Doppler data sequences. Each of the MTI filters 132 performs such a filtering process in correspondence with the channel thereof. In this situation, each of the MTI filters 132 performs the filtering process that eliminates signals representing a stationary state or a small movement. For example, each of the MTI filters 132 may be an Infinite Impulse Response (IIR) filter or may be a filter to perform a main component analysis such as that disclosed in Japanese Patent Application Laid-open No. 2014-158698.

Correcting circuitry 300 is configured to perform a correcting process to suppress side lobes occurring from highly-reflective members. Details of the correcting circuitry 300 will be explained later. A beam former 133 is configured to execute a beam forming function. In other words, the beam former 133 is configured to generate the reflected-wave data by performing a phasing addition process that uses the reflected-wave signal corresponding to each of the channels and resulting from the correcting process performed by the correcting circuitry 300. The beam former 133 outputs the generated reflected-wave data to the autocorrelation circuitry 134.

The autocorrelation circuitry 134 is configured to perform an autocorrelation calculation by using the reflected-wave data generated by the beam former 133. The calculating circuitry 135 is configured to estimate velocity (V), power (P), and dispersion (T) values of the blood flow signal. In other words, the calculating circuitry 135 is configured to calculate blood flow information from the second blood flow signal.

Incidentally, the mechanism of the occurrence of side lobes occurring from highly-reflective members when a blood flow image is displayed by performing the all-raster parallel simultaneous reception with the transmission of a plane wave or a diffuse wave had not been revealed. In addition, in Japanese Patent Application No. 2015-181125 and Japanese Patent Application No. 2015-181126, the present applicant proposed a method for reducing artifacts on the presumption that arc-shaped artifacts were caused by saturation of circuits. However, in subsequent research, the present applicant discovered that arc-shaped artifacts may occur even when circuits are not saturated and that artifacts become more prominent when circuits are saturated. In this regard, a mechanism of the occurrence of side lobes occurring from highly-reflective members when a blood flow image is displayed by performing the all-raster parallel simultaneous reception with the transmission of a plane wave or a diffuse wave will be explained. After that, a method for addressing the side lobes occurring from highly-reflective members will be explained.

First, prior to the explanation of the correcting process to suppress the side lobes occurring from highly-reflective members, the mechanism of the occurrence of artifacts will be explained. In the present example, to explain the mechanism of the occurrence of artifacts, a relationship between the signals that have passed through the MTI filters 132 and artifacts will be explained. FIGS. 6 to 9 are drawings for explaining the mechanism of the occurrence of the artifacts.

Figure 6:
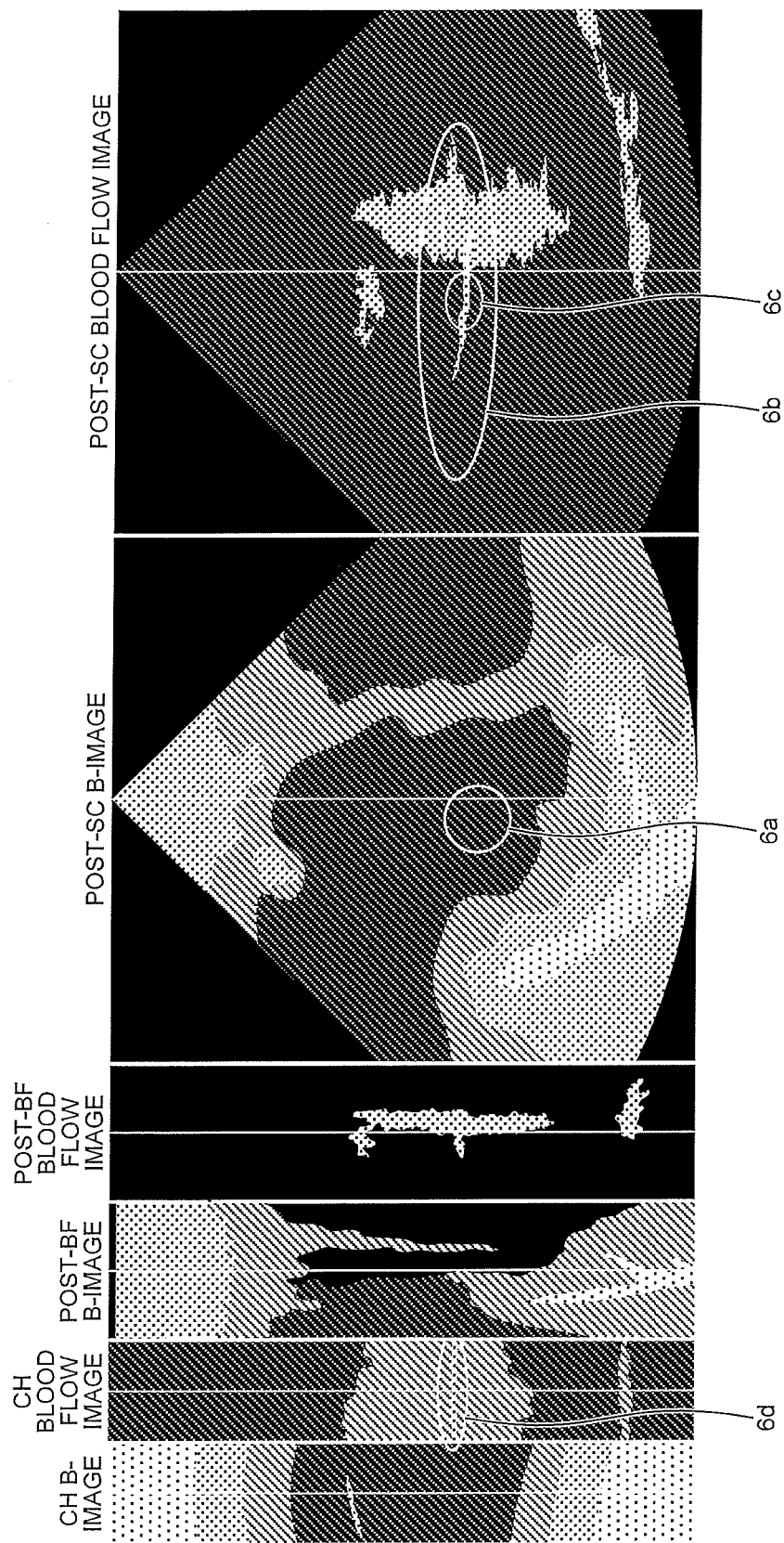
FIG. 6 is a drawing for explaining a mechanism of occurrence of artifacts.

FIG. 6 illustrates images in which an artifact is appearing in the image of the heart when a diffuse wave is transmitted by using a sector probe. All the images in FIG. 6 are displayed by performing a logarithmic compression process.

FIG. 6 illustrates, from the left to the right of the drawing page, a CH B-image, a CH blood flow image, a post-BF B-image, a post-BF blood flow image, a post-SC B-image, and a post-SC blood flow image.

The CH B-image is obtained by rendering, in an image, the amplitudes of the signals that correspond to the channels and that were output from the quadrature detecting circuit 203. The CH blood flow image is obtained by rendering, in an image, the amplitudes of the signals that have passed through the MTI filters 132. In the CH B-image and the CH blood flow image, the width direction indicates the channel direction, whereas the height direction indicates the depth (time). Further, although the CH blood flow image may be an image resulting from the logarithmic compression process, it is preferable to use an image of amplitudes prior to the logarithmic compression process, because the level of sensitivity in the straight line detection process (explained later) is higher.

The post-BF B-image is obtained by rendering, in an image, the signals resulting from the beam forming process performed by the beam former 204. The post-BF blood flow image is obtained by rendering, in an image, the signals resulting from the beam forming process performed by the beam former 133. The post-SC B-image is a B-mode image resulting from a coordinate transformation performed on the signals, to be suitable for the display 13. The post-SC blood flow image is a blood flow image resulting from a coordinate transformation performed on the signals, to be suitable for the display 13.

In this situation, a region 6a marked as an enclosure in the post-SC B-image in FIG. 6 indicates a valve of the heart. In a region 6b marked as an enclosure in the post-SC blood flow image in FIG. 6 exhibits occurrence of an arc-shaped artifact. Further, in the post-SC blood flow image, a region corresponding to the region 6a in the post-SC B-image is indicated as a region 6c. In FIG. 6, when the post-SC B-image is compared with the post-SC blood flow image, the arc-shaped artifact appearing in the post-SC blood flow image is in a positional relationship to overlap with the region 6a marked as the enclosure in the post-SC B-image. Accordingly, it is understood that the arc-shaped artifact appearing in the region 6b marked as the enclosure in the post-SC blood flow image is caused by the valve of the heart in the region 6c marked as the enclosure in the post-SC blood flow image.

Further, in the CH blood flow image in FIG. 6, a line 6d extending parallel to the channel direction is displayed. In this situation, because the line appearing in the CH blood flow image is not visible in the CH B-image, the line 6d in the CH blood flow image in FIG. 6 represents signals that have passed through the MTI filters 132. In other words, the line 6d in the CH blood flow image in FIG. 6 represents signals originating from a moving member. Further, from the post-SC B-image in FIG. 6, it is possible to identify the moving member as the valve of the heart.

Figure 7:
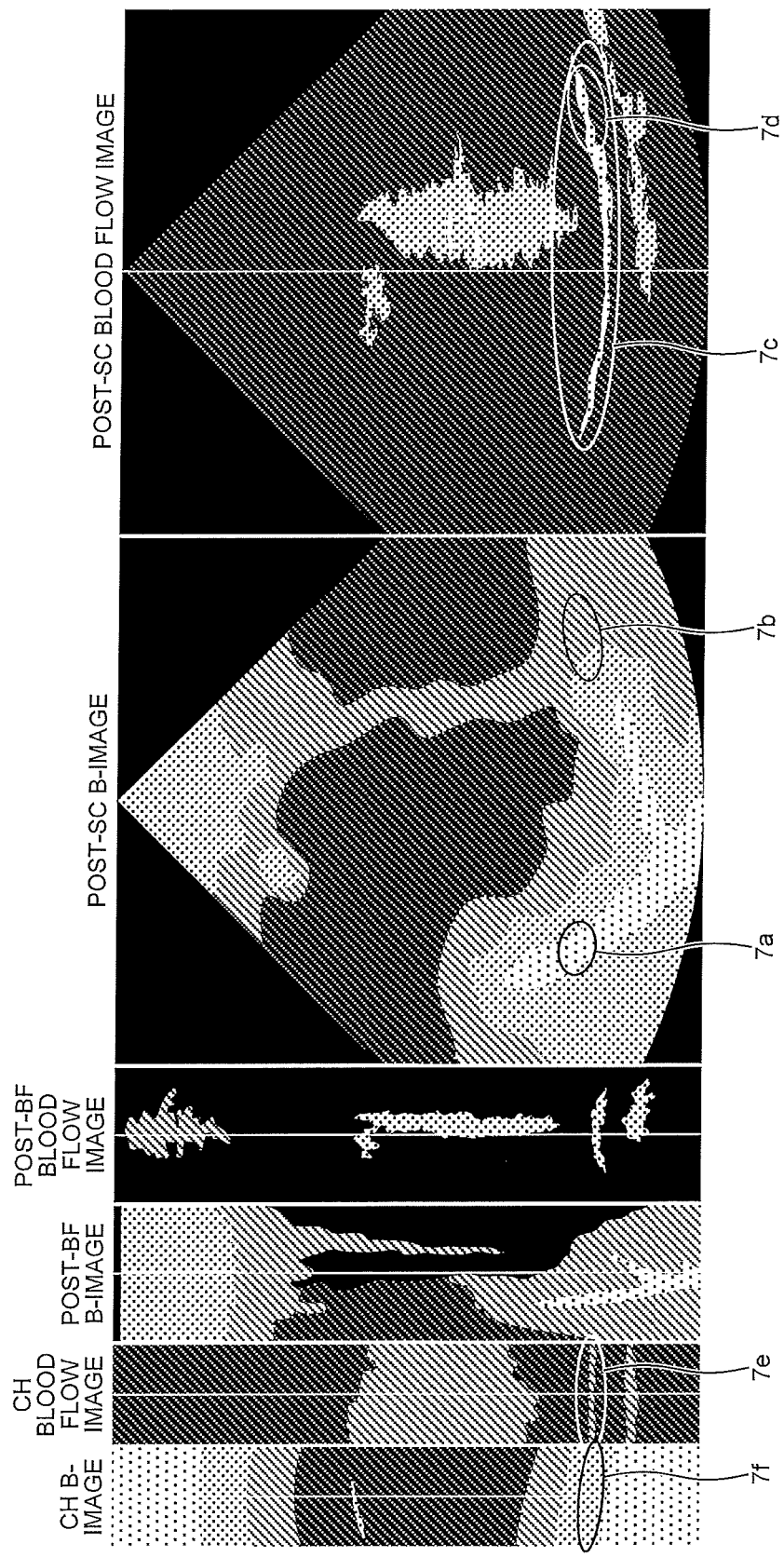
FIG. 7 is another drawing for explaining the mechanism of the occurrence of the artifacts.

Next, an example will be explained in which it is verified in another image whether a line displayed in the CH blood flow image in FIG. 6 shall always be a straight line extending parallel to the channel direction. Similarly to FIG. 6, FIG. 7 illustrates images in which an artifact is appearing in an image of the heart when a diffuse wave is transmitted by using a sector probe. All the images in FIG. 7 are displayed by performing a logarithmic compression process. Similarly to FIG. 6, FIG. 7 illustrates, from the left to the right of the drawing page, a CH B-image, a CH blood flow image, a post-BF B-image, a post-BF blood flow image, a post-SC B-image, and a post-SC blood flow image. Because the CH B-image, the CH blood flow image, the post-BF B-image, the post-BF blood flow image, the post-SC B-image, and the post-SC blood flow image illustrated in FIG. 7 are similar to the CH B-image, the CH blood flow image, the post-BF B-image, the post-BF blood flow image, the post-SC B-image, and the post-SC blood flow image in FIG. 6, detailed explanations thereof will be omitted.

In the post-SC B-image in FIG. 7, a cardiac wall 7a and a cardiac wall 7b each having a high level of brightness are rendered in substantially symmetrical positions on the left and the right with respect to the center of the image. Further, a region 7c marked as an enclosure in the post-SC blood flow image in FIG. 7 exhibits occurrence of an arc-shaped artifact. Further, in the post-SC blood flow image, a region corresponding to the region 7b in the post-SC B-image is indicated as a region 7d. The arc-shaped artifact appearing in the post-SC blood flow image is in a positional relationship to overlap with the cardiac wall 7b in the right side section of the post-SC B-image. Accordingly, it is understood that the arc-shaped artifact appearing in the post-SC blood flow image is caused by the section of the cardiac wall 7b positioned on the right side.

Further, in the CH blood flow image in FIG. 7, a line 7e extending parallel to the channel direction is rendered. In the present example, because the cardiac wall positioned on the left side is hardly visible in the post-SC blood flow image, it is understood that the line 7e extending parallel to the channel direction in the CH blood flow image in FIG. 7 appears due to a reflection echo from the cardiac wall on the right side.

In contrast, in the CH B-image in FIG. 7, signals sloping downward toward the right are rendered in a region 7f. In the post-SC B-image, because the intensities of the signals near the cardiac wall 7a on the left side are higher than those in the surroundings thereof, it is understood that the signals sloping downward toward the right appearing in the region 7f of the CH B-image are caused by the cardiac wall 7a positioned on the left side. As for the echo signals received at the channels from a reflection source located in the position of the cardiac wall 7a on the left side in the post-SC B-image, the channels positioned on the left side receive the reflected waves earlier because the distances from the reflection source are shorter, whereas the channels positioned on the right side receive the reflected waves later because the distances from the reflection source are longer. Accordingly, it is natural that the signals slope downward toward the right as indicated in the region 7f of the CH B-image.

Further, in the post-SC B-image in FIG. 7, as for the echo signals from a reflection source located in the position of the cardiac wall 7b on the right side, which is in a symmetrical position with the cardiac wall 7a on the left side, the channels positioned on the right side are supposed to receive the reflected waves earlier because the distances from the reflection source are shorter, whereas the channels positioned on the left side are supposed to receive the reflected waves later because the distances from the reflection source are longer, and the signals are supposed to slope downward toward the right. However, the echo signals from the reflection source located in the position of the cardiac wall 7b on the right side in the post-SC B-image are rendered as a horizontal straight line in the CH blood flow image in FIG. 7, contrary to the expectation.

In the explanation above, the reception echo from the reflection source is regarded as a spherical wave occurring from a point reflector such as that expected by a Delay And Sum (DAS) beam former. When a normal transmission focus is applied, an echo is primarily returned from a position on the transmission beam. Accordingly, it is natural to regard the reception echo from the reflection source as a spherical wave occurring from a point reflector. Further, even when a plane wave is transmitted or a diffuse wave is transmitted, it is acceptable to assume that an echo from a scatterer or a point reflector returns as a spherical wave from one certain point.

Figure 8:
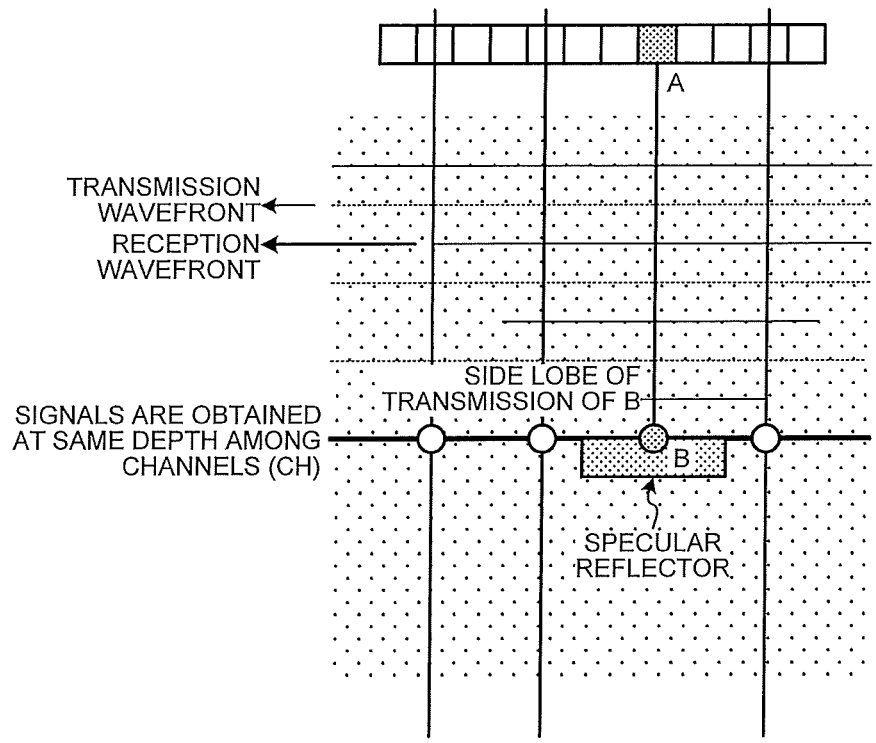
FIG. 8 is yet another drawing for explaining the mechanism of the occurrence of the artifacts.

Next, a reception echo in a situation where the reflection source is a specular reflector will be discussed. FIG. 8 illustrates an example in which, during a linear scan using a linear probe, a transmission wavefront of a plane wave becomes incident perpendicularly to the specular reflector and gets reflected. In FIG. 8, the transmission wavefront is indicated with a broken line, whereas the reception wavefront is indicated with a solid line. When the transmission wavefront becomes incident perpendicularly to the specular reflector and gets reflected, the reflection has a plane wave as indicated with the solid line. In this situation, even when the surface of the specular reflector is replaced with a set of a large number of point reflectors, it is understood that the leading end of the wavefront forms a straight line on the basis of the Huygens' principle. Strictly speaking, the transmission wavefront is diffracted at the end parts of the specular reflector, the diffraction of the transmission wavefront will be ignored in the present example.

As for the reception signal having a plane wave as described above, because the echo signals are input mutually at the same time (depth) among the channels, signal images corresponding to the channel form a pattern of a straight line extending parallel to the channel direction, as indicated in the CH blood flow image in FIG. 6 and the CH blood flow image in FIG. 7. In other words, the straight line extending parallel to the channel direction is due to the fact that, when the plane wave is transmitted, the reflection echo from the specular reflector has a plane wave and not a spherical wave. As for specular reflections, because a slight change in the angle can change the reflection direction, artifacts do not occur regularly, but an artifact occurs momentarily when the angles match exactly. This phenomenon can be observed in actuality. As additional information, when a diffuse wave is transmitted during a sector scan using a sector probe, as the situation prior to a coordinate transformation is taken into consideration, the mechanism is the same as that in the example illustrated in FIG. 8 where the plane wave is transmitted during the linear scan using the linear probe.

Figure 9:
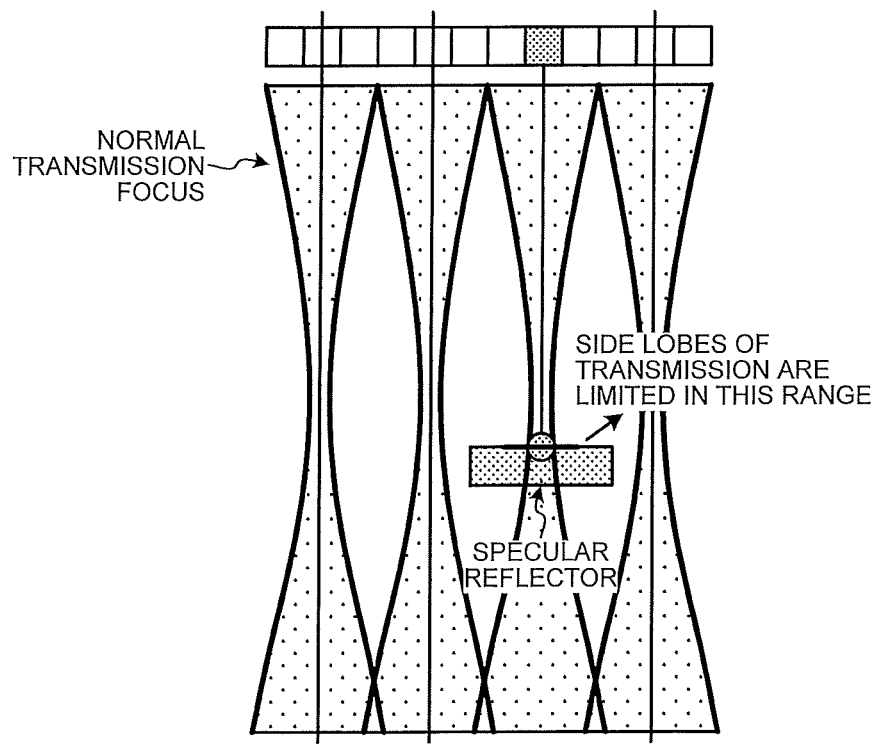
FIG. 9 is yet another drawing for explaining the mechanism of the occurrence of the artifacts.

Further, when a normal transmission focus is applied, even when the abovementioned artifact from the specular reflector has occurred, the problem will not be evident. FIG. 9 illustrates an example in which a normal transmission focus is applied. In the normal ultrasound transmission illustrated in FIG. 9, the transmission focus is applied to the same raster element as the reception raster element of the ultrasound wave, so that the reception is performed with one raster element with respect to one transmission. In other words, because a focus is applied by both the transmission and the reception, the side lobe level in the transmission and reception ultrasound field is low, and what is received is substantially only the reflected-wave signals from the reflector positioned over the raster elements. In that situation, because the signals from the specular reflector spread only within the transmission beam, even if artifacts appear, the artifacts appear only for the raster elements equal to or smaller than the quantity (usually 1 to 4) involved in the parallel simultaneous reception. In contrast, when the all-raster parallel simultaneous reception is performed as indicated in FIG. 8, because the transmission beam is the same, all the raster elements are affected, and an arc-shaped artifact occurs.

As explained above, when a plane wave is transmitted, in the situation where the reflection echo from the specular reflector has a plane wave, an artifact having the pattern of a straight line extending parallel to the channel direction occurs in the signal image corresponding to the channels. To cope with this situation, in the first embodiment, the Doppler processing circuitry 130 is configured to extract, prior to a beam forming process, the first blood flow signals corresponding to the plurality of channels from the reception signals corresponding to the channels while suppressing signals originating from tissues and to further extract the second blood flow signal by performing the beam forming process after suppressing, of the extracted first blood flow signals corresponding to the plurality of channels, a component in the predetermined direction. Alternatively, the Doppler processing circuitry 130 is configured to extract, prior to a beam forming process, the first blood flow signals corresponding to the plurality of channels from the reception signals corresponding to the channels while suppressing signals originating from tissues and to further extract the second blood flow signal by performing the beam forming process after suppressing, of the extracted first blood flow signals corresponding to the plurality of channels, one or more signals each having an amplitude equal to or larger than a predetermined threshold value.

Figure 10:
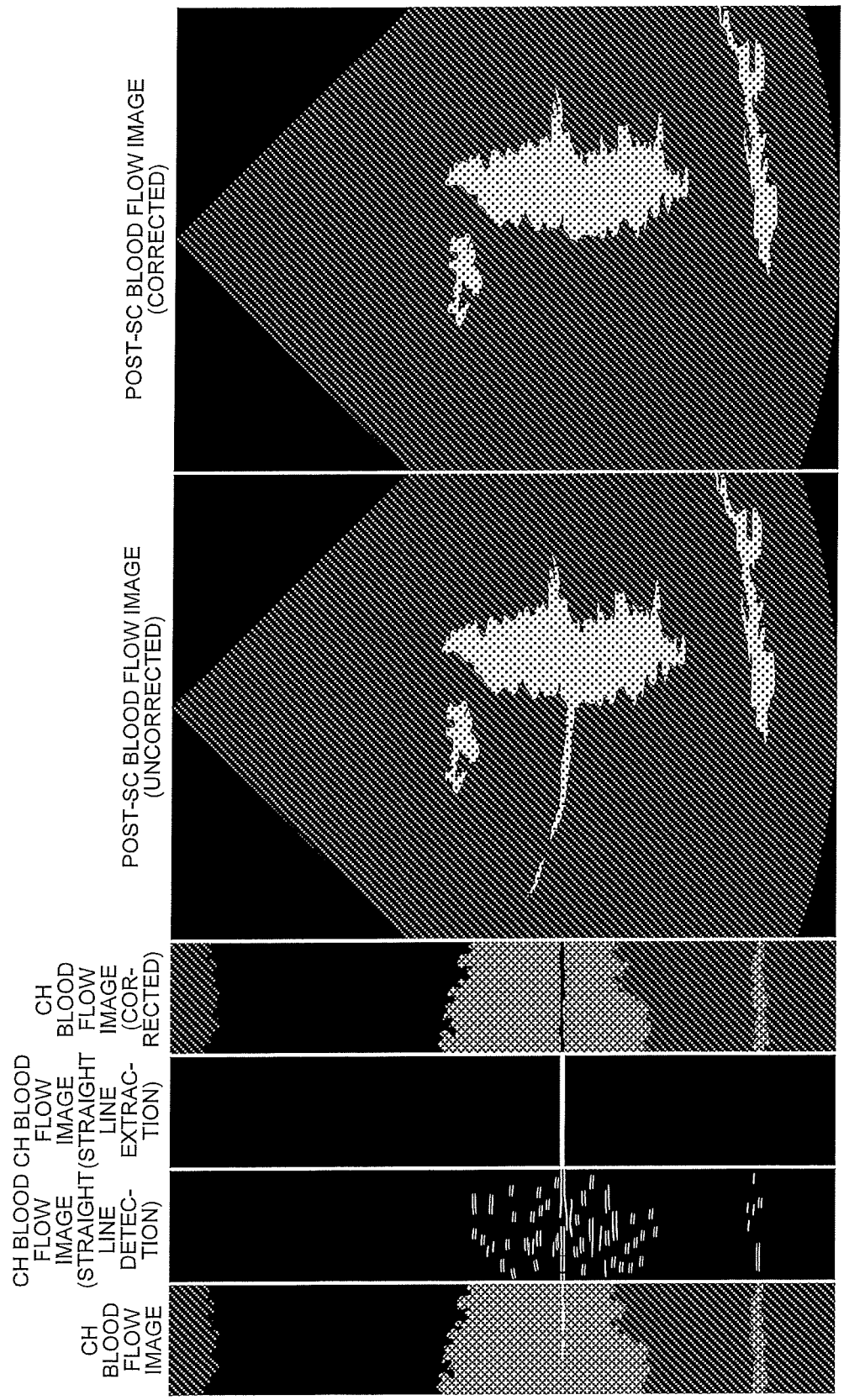
FIG. 10 is a drawing for explaining the first embodiment.

In the following sections, details of the process performed by the Doppler processing circuitry 130 according to the first embodiment will be explained. More specifically, the second blood flow signal extracting process to be performed on the signals resulting from the filtering process by the MTI filters 132 will be explained. FIGS. 10 to 13 are drawings for explaining the first embodiment. FIG. 10 illustrates images in which an artifact is appearing in an image of the heart when a diffuse wave is transmitted by using a sector probe. All the images in FIG. 10 are displayed by performing a logarithmic compression process.

FIG. 10 illustrates, from the left to the right of the drawing page, a CH blood flow image, a CH blood flow image (straight line detection), a CH blood flow image (straight line extraction), a CH blood flow image (corrected), a post-SC blood flow image (uncorrected), and a post-SC blood flow image (corrected). The image in FIG. 10 representing the CH blood flow image is the same as the CH blood flow images in FIGS. 6 and 7. In the CH blood flow images described below, the width direction corresponds to the CH (channel) direction, whereas the height direction corresponds to the depth (time). Further, although the CH blood flow images explained below with reference to the drawings are displayed by performing the logarithmic compression process for the purpose of facilitating the viewing, the CH blood flow images generated by the correcting circuitry 300 use amplitude signals on which no logarithmic compression process is performed.

Of the first blood flow signals corresponding to the plurality of channels, the correcting circuitry 300 is configured to suppress the component in the predetermined direction. For example, the correcting circuitry 300 generates a CH blood flow image from the first blood flow signals. In this situation, the correcting circuitry 300 generates the CH blood flow image by obtaining the amplitudes of the first blood flow signals that correspond to the channels and were output from the MTI filters 132.

After that, the correcting circuitry 300 detects the component in the predetermined direction from the CH blood flow image. For example, the correcting circuitry 300 applies a Sobel filter configured to detect a straight line extending parallel to the channel direction. In this situation, as the Sobel filter to detect the straight line extending parallel to the channel direction, a convolution process is performed on the coefficient matrix presented below in "Expression 1".

$$\begin{pmatrix} 1 & 1 & 1 & 1 & 1 \\ -1 & -1 & -1 & -1 & -1 \end{pmatrix} \qquad \text{(Expression 1)}$$

By applying the Sobel filter, the correcting circuitry 300 obtains the CH blood flow image (straight line detection) illustrated in FIG. 10. Subsequently, the correcting circuitry 300 binarizes the CH blood flow image (straight line detection) by performing an appropriate threshold value process thereon and further improves continuity by applying a morphology filter configured to perform an expansion process in the longitudinal direction to the binarized result. Accordingly, the correcting circuitry 300 obtains the CH blood flow image (straight line extraction) illustrated in FIG. 10. Further, although the example is explained above in which the correcting circuitry 300 uses the Sobel filter for detecting the straight line extending parallel to the channel direction, possible embodiments are not limited to this example. For instance, the correcting circuitry 300 may use any of publicly-known methods for detecting a straight line having a specific slope.

Figure 11:
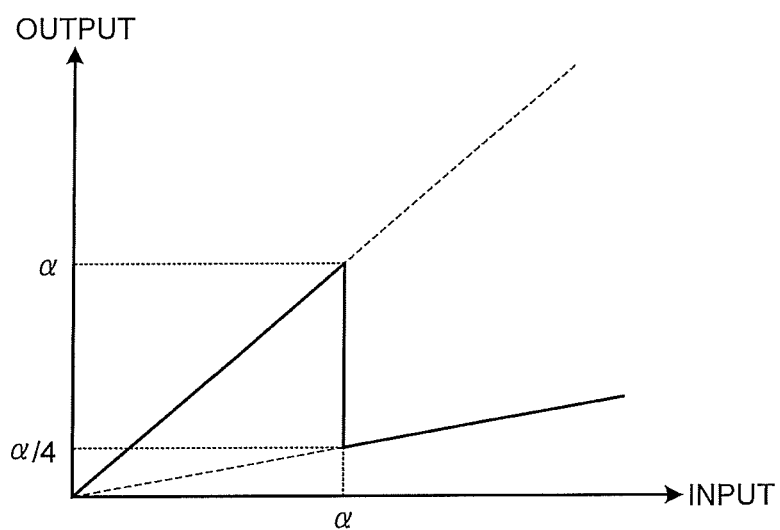
FIG. 11 is another drawing for explaining the first embodiment.

After that, of the extracted first blood flow signals corresponding to the plurality of channels, the correcting circuitry 300 suppresses the component in the predetermined direction. The suppressing process performed by the correcting circuitry 300 will be explained, with reference to FIG. 11. In FIG. 11, the horizontal axis expresses input values, whereas the vertical axis expresses output values. As illustrated in FIG. 11, with respect to the CH blood flow image (straight line extraction) in FIG. 10, when an input value is less than a, the correcting circuitry 300 outputs the input value, and when an input value is equal to or larger than a, the correcting circuitry 300 suppresses the signal. For example, the correcting circuitry 300 reduces to an input value to one-fourth (¼) (−12 dB). In other words, the correcting circuitry 300 exercises control so as to vary the suppressed values in accordance with the input values. As a result, it is possible to decrease unnatural changes in the gain in the image, depending on the position in which an artifact is occurring. As a result of the suppressing process performed in this manner, the correcting circuitry 300 obtains the CH blood flow image (corrected) illustrated in FIG. 10. The CH blood flow image (corrected) in FIG. 10 illustrates the example in which the correcting circuitry 300 suppresses the amplitude values in the detected region to −12 dB.

The beam former 133 is configured to extract the second blood flow signal by performing the beam forming process after suppressing, of the first blood flow signals corresponding to the plurality of channels, the component in the predetermined direction. The beam former 133 performs the beam forming process by implementing DAS.

Subsequent to the beam forming process performed by the beam former 133, the autocorrelation circuitry 134 performs an autocorrelation calculation in which the lags are 0 and 1. Further, the calculating circuitry 135 calculates velocity, dispersion, and power values of the blood flow signal as blood flow information. A coordinate transformation is performed on these signals by the image generating circuitry 140 in FIG. 1, and the result is stored into the image memory 150. Further, the processing circuitry 170 causes the display 13 to display a blood flow image. For example, the processing circuitry 170 causes the display 13 to display a power image of the blood flow signals resulting from the coordinate transformation, such as the image indicated as the post-SC blood flow image (corrected) in FIG. 10. Further, a blood flow image obtained by performing the beam forming process on the first blood flow signals that correspond to the channels and were output from the MTI filters 132 and calculating the blood flow information is illustrated in FIG. 10 as the post-SC blood flow image (uncorrected). In other words, the post-SC blood flow image (uncorrected) in FIG. 10 is a blood flow image generated without performing the second blood flow signal extracting process on the signals resulting from the filtering process by the MTI filters 132. When the post-SC blood flow image (uncorrected) is compared with the post-SC blood flow image (corrected), it is observed that the artifact appearing in the post-SC blood flow image (uncorrected) does not appear in the post-SC blood flow image (corrected). Further, in the post-SC blood flow image (corrected), because the region from which the straight line was extracted is arranged to have one-fourth (¼) (−12 dB) of the amplitude instead of zero (0), the continuity also seems natural.

Figure 12:
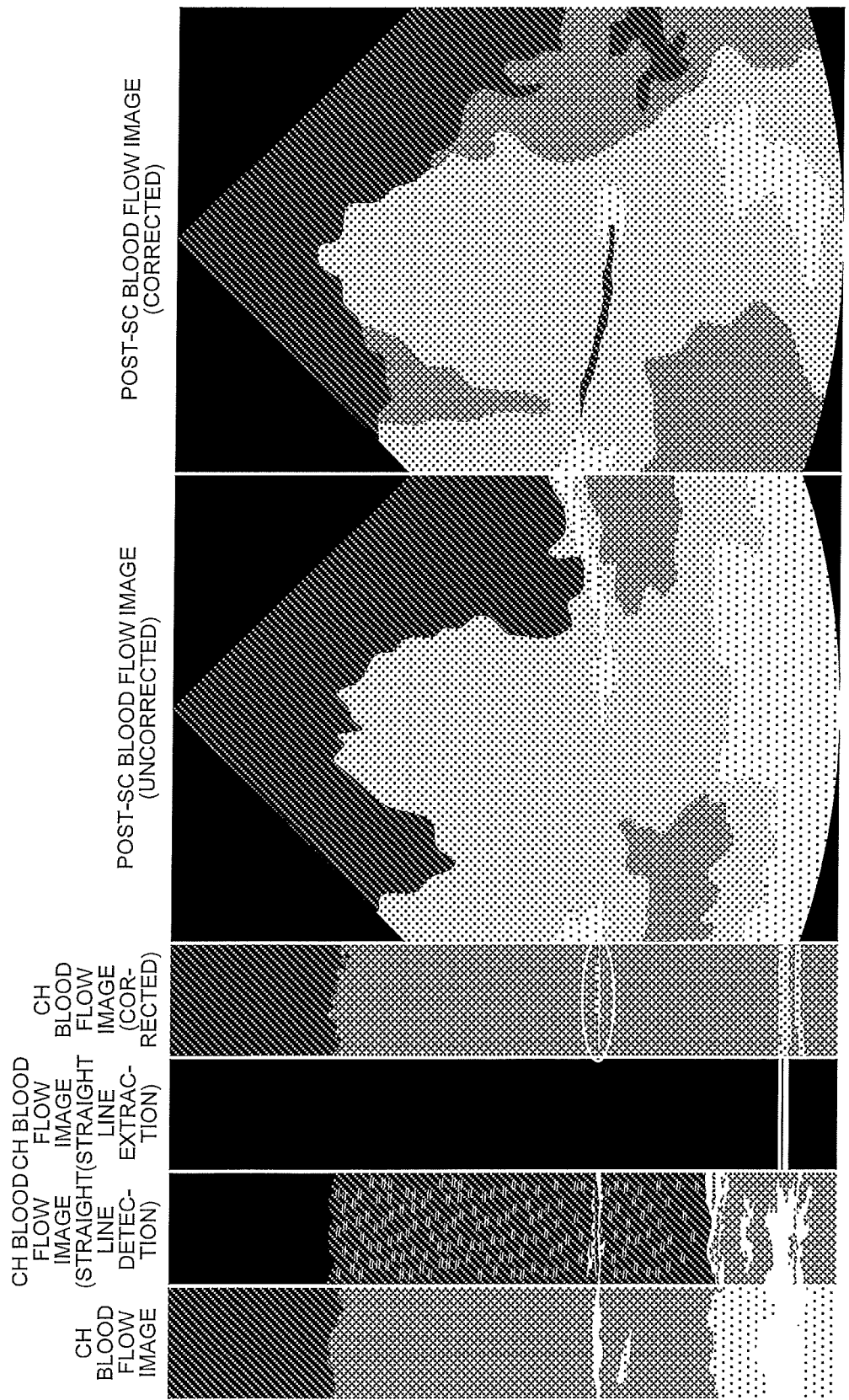
FIG. 12 is yet another drawing for explaining the first embodiment.

FIG. 12 illustrates another example of an image in which an artifact appears in an image of the heart, when a diffuse wave is transmitted by using a sector probe. FIG. 12 illustrates frames including signals originating from clutter components having significant movements. In this situation, all the images in FIG. 12 are displayed by performing a logarithmic compression process. Similarly to FIG. 10, FIG. 12 illustrates, from the left to the right of the drawing page, a CH blood flow image, a CH blood flow image (straight line detection), a CH blood flow image (straight line extraction), a CH blood flow image (corrected), a post-SC blood flow image (uncorrected), and a post-SC blood flow image (corrected).

The image indicated in FIG. 12 as the CH blood flow image is generated in the same manner as the CH blood flow images in FIGS. 6 and 7. In the CH blood flow images described below, the width direction corresponds to the channel direction, whereas the height direction corresponds to the depth (time). Further, although the CH blood flow images explained below with reference to the drawings are displayed by performing the logarithmic compression process for the purpose of facilitating the viewing, the CH blood flow images generated by the correcting circuitry 300 use amplitude signals on which no logarithmic compression process is performed.

The correcting circuitry 300 is configured to generate the CH blood flow image illustrated in FIG. 12 from the first blood flow signals. In this situation, the correcting circuitry 300 generates the CH blood flow image by obtaining the amplitudes of the first blood flow signals that correspond to the channels and were output from the MTI filters 132. In the present example, the levels of brightness of the CH blood flow image in FIG. 12 are considerably high. In that situation, there is a problem that many motion artifacts may occur in the post-SC blood flow image (uncorrected). At the same time, the image may have many side lobes having significant transversal streaks.

Failures in eliminating imaged tissues that may be observed after the passing through the MTI filters 132 may significantly vary among the channels depending on changes in the phases of movements and speckles. In that situation, for example, when a signal having a large amplitude remains only for one channel, a large side lobe occurs after the beam forming process is performed by implementing DAS. Like in this example, when a signal is originating from a tissue having a high reflection intensity and having a large movement such as a valve or a wall, and if the signal that fails to be eliminated after having passed through the MTI filters 132 has a large amplitude, a problem occurs in the post-SC blood flow image (uncorrected). To cope with this situation, by performing the process of reducing the amplitude and suppressing the high levels of brightness prior to the beam forming process that implements DAS, two advantageous effects can be expected where it is possible to reduce the motion artifacts and to reduce the side lobes.

Figure 13:
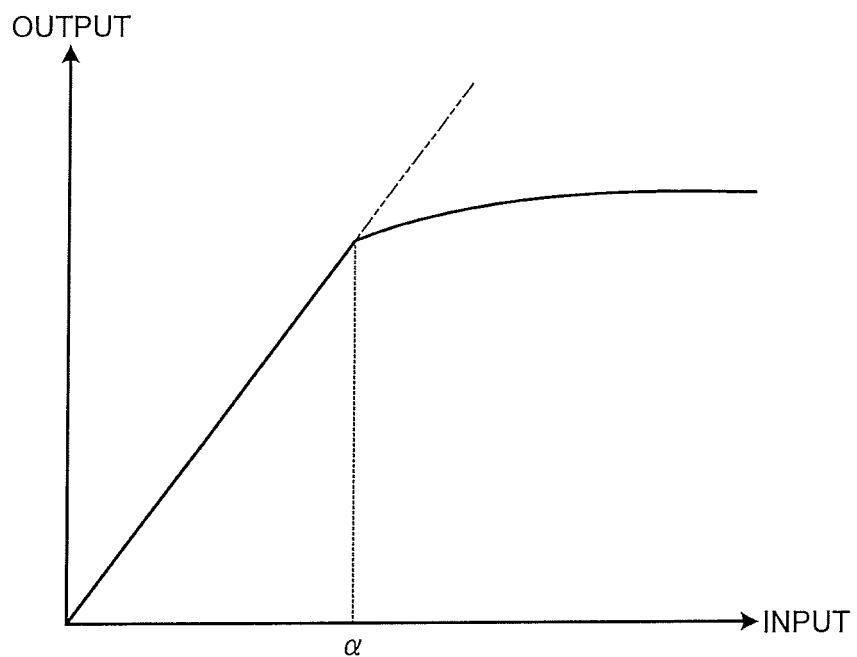
FIG. 13 is yet another drawing for explaining the first embodiment.

In FIG. 13, the horizontal axis expresses input values, whereas the vertical axis expresses output values. As illustrated in FIG. 13, with respect to signals of which the input values are each equal to or larger than a in the CH blood flow image in FIG. 12, the correcting circuitry 300 outputs output values obtained by suppressing the input values by using a predetermined method. In other words, the correcting circuitry 300 exercises control so as to vary the suppressed values in accordance with the input values. As a result, it is possible to decrease unnatural changes in the gain in the image, depending on the position in which an artifact is occurring. As a result of the suppressing process performed in this manner, the correcting circuitry 300 is able to reduce the amplitude in the CH blood flow image illustrated in FIG. 12. Further, as a result of the process of suppressing the high levels of brightness, the correcting circuitry 300 is able to arrange the threshold value used for detecting the straight line to be a certain percentage of a maximum value. It is therefore possible to apply a robust optimization to the process.

In the post-SC blood flow image (uncorrected) illustrated in FIG. 12, the arc-shaped artifact appearing in the image of the cardiac chamber is caused by the valve. However, in the CH blood flow image (straight line extraction), no straight line is detected in the section corresponding to the valve. In the post-SC blood flow image (corrected), artifacts are reduced in comparison to those in the post-SC blood flow image (uncorrected). The reduction of the artifacts is not an advantageous effect achieved by detecting and suppressing the straight line, but is an advantageous effect achieved by performing the process of suppressing the signals having high levels of brightness. In this manner, by suppressing such signals of which the output values from the MTI filters 132 corresponding to the channels are large, it is possible to reduce the side lobes and to reduce the artifacts. Further, in the post-SC blood flow image (uncorrected) in FIG. 12, also in the section having high levels of brightness due to a motion artifact of the cardiac wall rendered in the lower section of the image, the levels of brightness have been lowered and the motion artifact has significantly been reduced by the process of suppressing the high levels of brightness.

FIG. 14 is a flowchart illustrating a procedure in a process performed by the ultrasound diagnosis apparatus according to the first embodiment. With reference to FIG. 14, an example will be explained in which a blood flow image is displayed by implementing the ultrahigh-speed framerate method realized by applying the all-raster parallel simultaneous reception to the high framerate method. Step S1 in FIG. 14 is a step realized by the transmission circuitry 111. At step S1, the transmission circuitry 111 causes the ultrasound probe 11 to transmit an ultrasound wave having either a plane wave or a diffuse wave.

Step S2 is a step realized by the reception circuitry 112. At step S2, the reception circuitry 112 generates reception signals by receiving the reflected-wave signals. The reception circuitry 112 outputs the generated reception signals to the Doppler processing circuitry 130. As a result, the reception signals corresponding to the channels are each stored into one of the memories 131 corresponding to the relevant transducer element. In this situation, the reception circuitry 112 outputs the generated reception signals to the B-mode processing circuitry 120 via the beam former 204.

Steps S3 and S4 are steps realized by the MTI filters 132. At step S3, each of the MTI filters 132 obtains the reception signal of a corresponding one of the channels from a corresponding one of the memories 131. For example, the MTI filter 132-1 obtains a reception signal from the memory 131-1 corresponding to the transducer element-1. The MTI filter 132-N obtains a reception signal from the memory 131-N corresponding to the transducer element-N.

At step S4, the MTI filters 132 extract the first blood flow signals. For example, prior to the beam forming process, the MTI filters 132 extract the first blood flow signals corresponding to the plurality of channels from the reception signals corresponding to the channels while suppressing signals originating from tissues.

At step S5, the Doppler processing circuitry 130 performs the second blood flow signal extracting process. FIG. 15 is a flowchart illustrating a procedure in the second blood flow signal extracting process performed by the Doppler processing circuitry according to the first embodiment. The process illustrated in FIG. 15 corresponds to the process at step S5 in FIG. 14.

Steps S101 through S104 in FIG. 15 are steps realized by the correcting circuitry 300. At step S101, the correcting circuitry 300 generates a CH blood flow image from the first blood flow signals. In this situation, the correcting circuitry 300 generates the CH blood flow image by obtaining the amplitudes of the first blood flow signals that correspond to the channels and were output from the MTI filters 132.

At step S102, the correcting circuitry 300 suppresses one or more signals each having an amplitude equal to or larger than the predetermined threshold value. For example, with respect to the signals of which the input values in the CH blood flow image are each equal to or larger than the predetermined threshold value, the correcting circuitry 300 outputs output values suppressed by multiplying the input values by a predetermined ratio. In other words, of the first blood flow signals corresponding to the plurality of channels, the correcting circuitry 300 suppresses the one or more signals each having an amplitude equal to or larger than the predetermined threshold value.

At step S103, the correcting circuitry 300 detects the component in the predetermined direction. For example, the correcting circuitry 300 applies a Sobel filter configured to detect a straight line extending parallel to the channel direction, to the CH blood flow image. In this situation, as the Sobel filter configured to detect the straight line extending parallel to the channel direction, the correcting circuitry 300 performs a convolution process on the coefficient matrix presented above in "Expression 1". After that, the correcting circuitry 300 binarizes the output by performing an appropriate threshold value process thereon and further improves continuity by applying a morphology filter configured to perform an expansion process in the longitudinal direction to the binarized result.

At step S104, of the extracted first blood flow signals corresponding to the plurality of channels, the correcting circuitry 300 suppresses the component in the predetermined direction. At step S105, the beam former 133 extracts the second blood flow signal by performing the beam forming process after suppressing, of the first blood flow signals corresponding to the plurality of channels, the component in the predetermined direction.

Step S105 is a step realized by the beam former 133. The beam former 133 performs the beam forming process by implementing DAS. In other words, the beam former 133 extracts the second blood flow signal by performing the beam forming process after suppressing, of the first blood flow signals corresponding to the plurality of channels, one or more signals each having an amplitude equal to or larger than the threshold value and subsequently suppressing the component in the predetermined direction. In this situation, the correcting circuitry 300 may omit one selected from between the process at step S102 and the process at steps S103 and S104 illustrated in FIG. 15. In other words, the beam former 133 may extract the second blood flow signal by performing the beam forming process after suppressing, of the first blood flow signals corresponding to the plurality of channels, the component in the predetermined direction. Alternatively, the beam former 133 may extract the second blood flow signal by performing the beam forming process after suppressing, of the first blood flow signals corresponding to the plurality of channels, one or more signals each having an amplitude equal to or larger than the predetermined threshold value.

Returning to the description of FIG. 14, step S6 is a step realized by the calculating circuitry 135. At step S6, the calculating circuitry 135 calculates blood flow information from the second blood flow signal. For example, as the blood flow information, the calculating circuitry 135 estimates velocity (V), power (P), and dispersion (T) values of the blood flow signal.

Step S7 is a step realized by the image generating circuitry 140. At step S7, the image generating circuitry 140 generates a blood flow image from the blood flow information. Step S8 is a step realized by the processing circuitry 170. At step S8, the processing circuitry 170 causes the display 13 to display the blood flow image.

In this situation, when the framerate of the ultrasound scan is 6,000 fps, while the display rate is 60 fps, the information displayed on the display 13 in a real-time manner is a small number of frames among the frames obtained from the ultrasound scan. Accordingly, when the operator wishes to observe flows of blood in the heart, the processing circuitry 170 freezes the ultrasound scan and subsequently plays back the information in a slow mode, at 6,000 fps or at 600 fps where the frames are thinned out to one-tenth (1/10). With this arrangement, the operator is able to visually observe the flows of blood. When the information is played back in the slow mode in this manner, it is necessary to obtain images at 6,000 fps or 600 fps. In that situation, the processing circuitry 170 may generate as many images as the required number of frames in a real-time manner or may arrange the data corresponding to one heartbeat to be stored in the memories 131 so as to generate images corresponding to the one heartbeat after a freezing operation.

Instead of displaying the images in slow motion after the ultrasound scan is frozen, the processing circuitry 170 may cause the display 13 to display, while the ultrasound waves are being transmitted and received, the blood flow images corresponding to one heartbeat over a time period calculated by multiplying a time period required by one heartbeat by a predetermined coefficient. For example, by using a method such as that disclosed in Japanese Patent Application Laid-open No. 2001-178723, the processing circuitry 170 may display, during a scan, images in slow motion slowed by N times, by displaying images during one heartbeat over a time period of N heartbeats.

Further, the processing circuitry 170 may identify a two-dimensional vector indicating a flow of blood by tracking a movement of a speckle between blood flow images and cause the display 13 to display the identified two-dimensional vector. For example, the processing circuitry 170 tracks the movement of the speckle in the blood by implementing a cross correlation method on images at 6,000 fps or images thinned out to 600 fps, so as to display the flow of blood with the two-dimensional vector.

As explained above, the ultrasound diagnosis apparatus 1 according to the first embodiment is configured to extract, prior to the beam forming process, the first blood flow signals corresponding to the plurality of channels from the reception signals corresponding to the channels while suppressing the signals originating from the tissues and to further extract the second blood flow signal by performing the beam forming process after suppressing, of the extracted first blood flow signals corresponding to the plurality of channels, the component in the predetermined direction. Alternatively, the ultrasound diagnosis apparatus 1 according to the first embodiment is configured to extract, prior to the beam forming process, the first blood flow signals corresponding to the plurality of channels from the reception signals corresponding to the channels while suppressing the signals originating from the tissues and to further extract the second blood flow signal by performing the beam forming process after suppressing, of the extracted first blood flow signals corresponding to the plurality of channels, one or more signals each having an amplitude equal to or larger than the threshold value. As a result, according to the first embodiment, when either a plane wave or a diffuse wave is transmitted, it is possible to reduce the artifacts caused by the specular reflector. As a result, it is possible to cause the display 13 to display the blood flow image that is less impacted by artifacts.

Further, in the first embodiment, in the CH blood flow image resulting from the filtering process performed by the MTI filters 132, the signals forming the straight line extending in the horizontal direction are suppressed. As a result, according to the first embodiment, it is possible to reduce the transmission side lobes caused by the specular reflection.

Further, in the first embodiment, in the CH blood flow image resulting from the filtering process performed by the MTI filters 132, the one or more signals each having a large amplitude are suppressed. As a result, according to the first embodiment it is possible to reduce the transmission side lobes caused by the highly-reflective member.

Further, in CH blood flow images, scatter echo from a scatterer does not appear as a clear line. In CH blood flow images, a clear straight line is rendered only by specular reflection echo. For this reason, the embodiment described above functions effectively in blood flow images. It should be noted that it may be difficult, in some situations, to apply the embodiment described above to B-mode images.

Further, according to the MV method, the APES method, and the PCI method, an adaptive beam forming process is performed on the signals resulting from the reception delay, before the adding process is performed thereon. However, because signals from a specular reflector have a plane wave, the phases cannot be aligned, when a normal reception delay based on a spherical wave is applied. For this reason, when the MV method, the APES method, or the PCI method is implemented, it is not possible to reduce artifacts caused by specular reflections.

A Modification Example of the First Embodiment

In the embodiment described above, the example is explained in which the plane wave becomes incident perpendicularly to the specular reflector, when the plane wave transmission is performed by using a linear probe or when the diffuse wave transmission is performed by using a sector probe. In that situation, the component of the reception signals representing the straight line extending parallel to the channel direction is the cause of the artifact in the blood flow image. Incidentally, when a plane wave transmission is performed by using a linear probe, the plane wave may become incident to the specular reflector at an angle in some situations. To cope with this situation, an example in which a plane wave becomes incident to a specular reflector at an angle is illustrated in FIG. 16. FIG. 16 is a drawing for explaining a modification example of the first embodiment.

FIG. 16 illustrates twelve transducer elements that are among the transducer elements included in the ultrasound probe 11. Further, FIG. 12 illustrates an example in which a specular reflector is positioned at an angle with respect to the channel direction of the transducer elements. In FIG. 16, the transmission wavefront is indicated with a broken line, whereas the reception wavefront is indicated with a solid line. As illustrated in FIG. 16, when the plane wave becomes incident to the specular reflector at an angle, the reception wavefront is a wavefront positioned at an angle with respect to the channel direction of the transducer elements. In this situation, when it is impossible to receive the wavefront reflected at an angle with the reception channels in the reception opening, the problem of artifacts will not occur. However, when it is possible to receive the wavefront reflected at an angle with the reception channels in the reception opening, the problem of artifacts will occur.

For example, when the wavefront reflected at an angle is positioned within the reception opening, the signals from the specular reflector are rendered in the CH blood flow image as a diagonal straight line. For this reason, the correcting circuitry 300 is configured to detect not only straight lines extending parallel to the channel direction, but also straight lines having a slope in a certain range. In other words, as the component in the predetermined direction, the correcting circuitry 300 extracts such a component of which the slope with respect to the channel direction forms a straight line within the predetermined range. More specifically, the correcting circuitry 300 applies a plurality of Sobel filters having mutually-different straight line detection directions and further calculates a logical sum of the results. In this situation, the correcting circuitry 300 may use any of publicly-known methods for detecting a straight line having a specific slope. Further, the correcting circuitry 300 suppresses the extracted component in the first blood flow signals.

As a means for realizing the first embodiment described above, either a hardware scheme or a software scheme may be used. For example, when the first embodiment is realized with software, at a stage subsequent to the reception circuitry and prior to the Doppler processing circuitry, a beam former having functions corresponding to those of the MTI filters 132, the correcting circuitry 300, and the beam former 133 is disposed. The beam former includes, for example, processing circuitry and a memory and is configured to execute the functions corresponding to those of the MTI filters 132, the correcting circuitry 300, and the beam former 133, by reading the programs stored in the storage circuitry 160, for example.

In the explanation above, the reception circuitry and the Doppler processing circuitry are each described as being configured with hardware; however, it is also acceptable to have a part of the processing performed by software, instead of having all of the processing performed by hardware. More specifically, the processes performed by the MTI filters 132, the correcting circuitry 300, the beam former 133, the autocorrelation circuitry 134, and the calculating circuitry 135 in FIG. 5 may be performed by software.

Further, when the beam forming process is performed by software, there will be no need for the Doppler processing circuitry 130 to include the same pieces of hardware in correspondence with the channels. The software may be configured to operate under a CPU, a Digital Signal Processor (DSP), or a GPU. Further, the process having the largest load when the beam forming process is performed by software is the process realized by the beam former 133.

In this situation, let us assume that the framerate achieved by the all-raster parallel simultaneous reception is 6,000 fps. Further, let us assume that the rate at which the images are structured by the image generating circuitry 140 and displayed by the display 13 is 60 fps. In that situation, it is sufficient when the beam former performs the beam forming process at 60 fps. Accordingly, it is possible to reduce the processing in the beam forming process to one-hundredth (1/100). In other words, the beam former arranges the cycle in which the beam forming process is performed to be longer than the cycle in which each frame is scanned.

Incidentally, according to a conventional technique by which a beam forming process is performed within reception circuitry so as to output reception signals to Doppler processing circuitry, the rate for the beam forming process needs to be 6,000 fps, which is equal to the framerate. According to the conventional technique, because the beam forming process is performed on the reception signal corresponding to each of the channels, the Doppler processing circuitry is a single system configured to process one reception signal.

In contrast, the Doppler processing circuitry 130 according to the first embodiment is structured with the plurality of systems configured to process the reception signals corresponding to the number of channels. For example, when the number of channels is 100, the processing performed by the MTI filters 132 would require a time period that is 100 times longer than the time period required by the conventional technique. However, when the Doppler processing circuitry 130 according to the first embodiment is realized with software by disposing the beam former, because it is possible to reduce the processing in the beam forming process to one-hundredth (1/100), it is possible to shorten the processing time to one-hundredth (1/100). Accordingly, by disposing the beam former, even when the processing of the MTI filters 132 is performed for each of the channels, it is possible to reduce the processing load in comparison to that in the conventional technique.

Second Embodiment

In the first embodiment, the straight line that extends parallel to the channel direction and is caused by the specular reflection is detected from the blood flow channel image. In this regard, when blood flow signals in a cardiac chamber and specular reflection signals from a valve are both present, it may be difficult in some situations to detect a straight line from a CH blood flow image.

To cope with this situation, as a second embodiment, an example will be explained in which the straight line is more easily detected by separating blood flow signals from specular reflection signals, through a Fourier transform (a Fast Fourier Transform [FFT]) performed in the channel direction on the first blood flow signals (IQ signals, and not a CH blood flow image).

An overall configuration of the ultrasound diagnosis apparatus 1 according to the second embodiment is almost the same as the overall configuration of the ultrasound diagnosis apparatus 1 according to the first embodiment illustrated in FIG. 1, except that a part of the functions of the correcting circuitry 300 is different. Thus, explanations thereof will be omitted. In the second embodiment, similarly to the first embodiment, an example will be explained in which blood flow images are displayed by implementing the ultrahigh-speed framerate method realized by applying the all-raster parallel simultaneous reception to the high framerate method. Further, similarly to the first embodiment, the transmission circuitry 111 is configured to cause the ultrasound probe 11 to perform an ultrasound scan that uses data sequences between frames as Doppler data sequences, under the control of the processing circuitry 170. Further, the transmission circuitry 111 is configured to control a plurality of transducer elements included in the ultrasound probe 11 so as to transmit either an ultrasound wave having a plane wave or an ultrasound wave having a diffuse wave. Further, the reception circuitry 112 is configured to cause the ultrasound probe 11 to perform an ultrasound scan in which the reflected-wave signals are received mutually at the same time by the plurality of transducer elements that transmitted the ultrasound wave.

Figure 17:
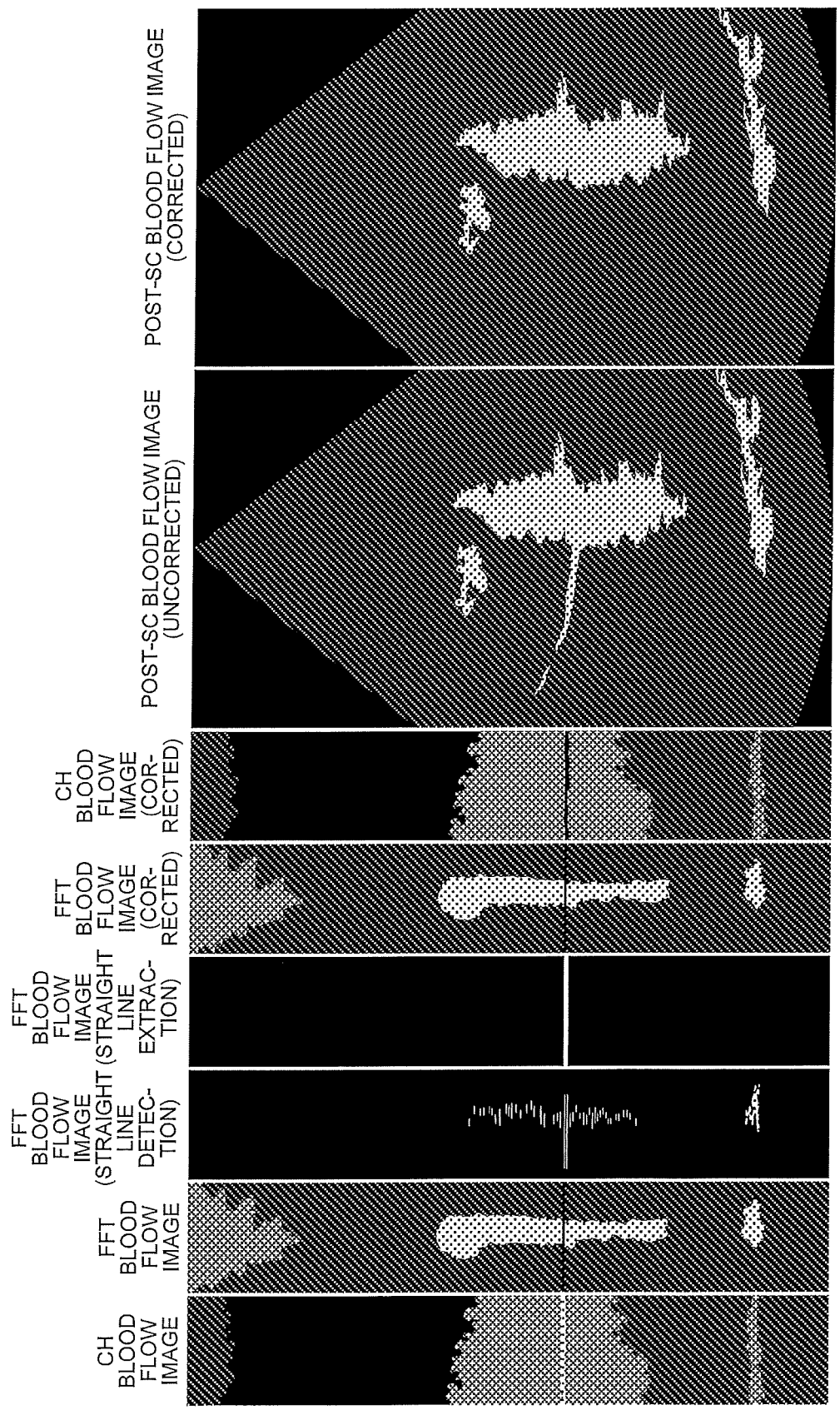
FIG. 17 is a drawing for explaining a second embodiment.

FIG. 17 is a drawing for explaining the second embodiment. All the images in FIG. 17 are displayed by performing a logarithmic compression process. FIG. 17 illustrates, from the left to the right of the drawing page, a CH blood flow image, an FFT blood flow image, an FFT blood flow image (straight line detection), an FFT blood flow image (straight line extraction), an FFT blood flow image (corrected), a CH blood flow image (corrected), a post-SC blood flow image (uncorrected), and a post-SC blood flow image (corrected). In the FFT blood flow images described below, the width direction corresponds to the channel direction, whereas the height direction corresponds to the depth (time). Further, although the CH blood flow images explained below with reference to the drawings are displayed by performing the logarithmic compression process for the purpose of facilitating the viewing, the CH blood flow images generated by the correcting circuitry 300 use amplitude signals on which no logarithmic compression process is performed.

The correcting circuitry 300 obtains first blood flow signals (IQ signals) corresponding to the channels from the MTI filters 132. Further, the correcting circuitry 300 generates an FFT blood flow image (which may also be referred to as a first conversion signal) by performing a Fourier transform in the channel direction on the first blood flow signals (the IQ signals) that correspond to the channels and were output from the MTI filters 132. Although the correcting circuitry 300 does not necessarily have to generate a CH blood flow image from the first blood flow signals that correspond to the channels and were obtained from the MTI filters 132, FIG. 17 illustrates the CH blood flow image for a reference purpose.

Subsequently, the correcting circuitry 300 detects a component in a predetermined direction from the FFT blood flow image. In this situation, for example, as the component in the predetermined direction, the correcting circuitry 300 extracts such a component of which the slope with respect to the channel direction forms a straight line within a predetermined range, from the first conversion signal. More specifically, the correcting circuitry 300 applies a Sobel filter configured to detect a straight line extending parallel to the channel direction. As the Sobel filter configured to detect the straight line extending parallel to the channel direction, the correcting circuitry 300 performs a convolution process on the coefficient matrix presented above in "Expression 1". As a result of the application of the Sobel filter, the correcting circuitry 300 obtains the FFT blood flow image (straight line detection) illustrated in FIG. 17. After that, the correcting circuitry 300 binarizes the FFT blood flow image (straight line detection) by performing an appropriate threshold value process thereon and further improves continuity by applying a morphology filter configured to perform an expansion process in the longitudinal direction to the binarized result.

As a result, the correcting circuitry 300 obtains the FFT blood flow image (straight line extraction) illustrated in FIG. 17. Although the example is explained in which the correcting circuitry 300 uses the Sobel filter for detecting the straight line extending parallel to the channel direction, possible embodiments are not limited to this example. For instance, the correcting circuitry 300 may use any of publicly-known methods for detecting a straight line having a specific slope.

After that, the correcting circuitry 300 suppresses the component in the predetermined direction in the FFT blood flow image. In other words, the correcting circuitry 300 suppresses the extracted component in the first conversion signal. As a result, the correcting circuitry 300 obtains the FFT blood flow image (corrected) illustrated in FIG. 17. In this situation, the correcting circuitry 300 suppresses the component in the predetermined direction in the FFT blood flow image, in the same manner as in the suppressing process explained with reference to FIG. 11. Subsequently, the correcting circuitry 300 obtains the CH blood flow image (corrected) by performing an inverse Fourier transform (Inverse FFT [IFFT]) on the FFT blood flow image (corrected) and rendering the amplitudes of the obtained signals into an image in the channel direction.

The beam former 133 is configured to extract a second blood flow signal by suppressing the component in the predetermined direction in the first conversion signal and subsequently performing an inverse Fourier transform before performing a beam forming process. In this situation, the post-SC blood flow image (uncorrected) in FIG. 17 is an image obtained by performing a beam forming process and a coordinate transformation on the CH blood flow image. The post-SC blood flow image (corrected) is an image obtained by performing a beam forming process and a coordinate transformation on the CH blood flow image (corrected). It is observed that, in the post-SC blood flow image (corrected), the artifacts from the valve have been eliminated.

Further, it is easier to extract a straight line from the FFT blood flow image than to extract a straight line from the CH blood flow image. More specifically, when a Fourier transform is performed in the channel direction on the first blood flow signals obtained by transmitting a diffuse wave while using a sector probe, signals as if a beam forming process was performed are obtained. When the source of echo is positioned sufficiently distant, because the Fraunhofer approximation is applicable, it is possible to obtain an echo source distribution by performing a Fourier transform on an aperture distribution. Even when the source of echo is not positioned sufficiently distant, it is possible to obtain an echo source distribution by performing a Fourier Transform, more than from a CH blood flow image. Accordingly, although the blood flow signals are widely distributed in the CH blood flow image, it is possible to limit the blood flow signals in a region close to the echo source distribution as observed in the FFT blood flow image. In contrast, because specular reflection signals return as plane waves, it is not possible to obtain an echo source distribution image by performing a Fourier transform. Further, because the phases change between the channels, images have a straight line extending over all the frequency regions. Further, it is possible to obtain an image close to the echo source distribution by performing a Fourier transform in the channel only when a diffuse wave transmission is performed by using a sector probe. When a plane wave transmission is performed by using a linear probe, it is not possible to obtain an image close to the echo source distribution.

Figure 18:
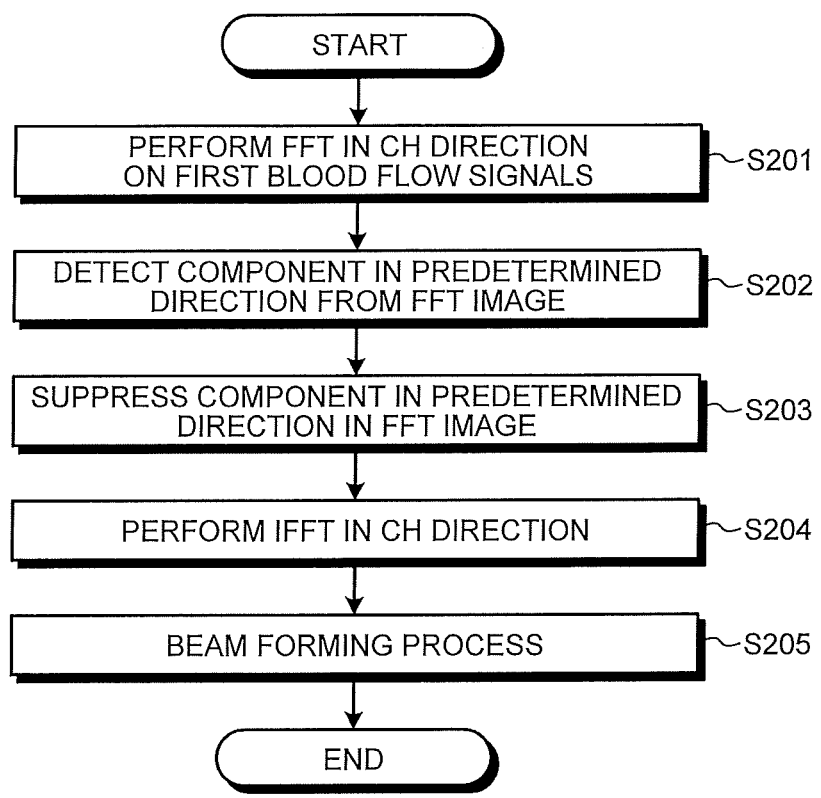
FIG. 18 is a flowchart illustrating a procedure in a second blood flow signal extracting process performed by Doppler processing circuitry according to the second embodiment.

Next, a procedure in a process performed by an ultrasound diagnosis apparatus according to the second embodiment will be explained. The procedure in the process performed by the ultrasound diagnosis apparatus according to the second embodiment is almost the same as the procedure in the process illustrated in FIG. 14, except for the difference from the second blood flow signal extracting process at step S5 in FIG. 14. For this reason, the following explanations fill focus on the second blood flow signal extracting process according to the second embodiment. FIG. 18 is a flowchart illustrating a procedure in the second blood flow signal extracting process performed by Doppler processing circuitry according to the second embodiment. The processes illustrated in FIG. 18 correspond to the process at step S5 in FIG. 14.

Steps S201 through S205 in FIG. 18 are steps realized by the correcting circuitry 300. At step S201, the correcting circuitry 300 generates the first conversion signal by performing an FFT in the channel direction on the first blood flow signals. In this situation, the correcting circuitry 300 performs the FFT in the channel direction on the first blood flow signals that correspond to the channels and were output from the MTI filters 132. As a result, the correcting circuitry 300 obtains the FFT blood flow image illustrated in FIG. 17.

At step S202, the correcting circuitry 300 detects a component in a predetermined direction. For example, the correcting circuitry 300 applies a Sobel filter configured to detect a straight line extending parallel to the channel direction, to the first conversion signal. In this situation, as the Sobel filter configured to detect the straight line extending parallel to the channel direction, the correcting circuitry 300 performs a convolution process on the coefficient matrix presented above in "Expression 1". As a result, as the first conversion signal, the correcting circuitry 300 obtains the FFT blood flow image (straight line detection) illustrated in FIG. 17. Subsequently, the correcting circuitry 300 binarizes the output by performing an appropriate threshold value process thereon and further improves continuity by applying a morphology filter configured to perform an expansion process in the longitudinal direction to the binarized result. Accordingly, the correcting circuitry 300 obtains the FFT blood flow image (straight line extraction) illustrated in FIG. 17.

At step S203, the correcting circuitry 300 suppresses the component in the predetermined direction in the first conversion signal. For example, the correcting circuitry 300 obtains the FFT blood flow image (corrected) illustrated in FIG. 17. At step S204, the correcting circuitry 300 performs an IFFT in the channel direction on the first conversion signal in which the component in the predetermined direction has been suppressed. From the result, the correcting circuitry 300 obtains a CH blood flow image (corrected) by performing an inversed Fourier transform on the FFT blood flow image (corrected) and rendering the amplitudes of the obtained signals into an image in the channel direction.

Step S205 is a step realized by the beam former 133. At step S205, the beam former 133 extracts the second blood flow signal by performing a beam forming process on the CH blood flow image (corrected) illustrated in FIG. 17. The beam former 133 performs the beam forming process by implementing DAS. In this situation, prior to the process at step S201, the correcting circuitry 300 may further perform the suppressing process at step S102 in FIG. 15.

As explained above, in the second embodiment, the blood flow signals and the specular reflection signals are separated from each other by performing the Fourier transform in the channel direction on the first blood flow signals, so as to make it easier to detect the straight line. As a result, according to the second embodiment, for example, even when the blood flow signals in the cardiac chamber and the specular reflection signals from the valve are both present, it is possible to detect the straight line from the CH blood flow image. As a result, according to the second embodiment, it is possible to reduce the artifacts caused by the highly-reflective member.

Third Embodiment

In the second embodiment, the example is explained in which the signals in the straight line part are suppressed by performing the Fourier transform in the channel direction on the first blood flow signals, and subsequently, the inverse Fourier transform is performed to perform the beam forming process by implementing DAS. Incidentally, it is known to be possible to perform a beam forming process by performing a two-dimensional Fourier transform while regarding reception signals that correspond to channels and that were obtained by transmitting a plane wave or a diffuse wave at a time, as two-dimensional signals in the time direction and the channel direction, and subsequently, a coordinate transformation is performed in a two-dimensional frequency space before performing a two-dimensional inverse Fourier transform (Reference Document 1: Garcia et al, "Stolt's f-k migration for plane wave ultrasound imaging", IEEE Transactions on Ultrasonics, Ferroelectrics, and Frequency Control, 2013, Vol. 60, No. 9, pp. 1853-1867; and Reference Document 2: Specification of U.S. Pat. No. 6,685,641).

Accordingly, when a Fourier transform has been performed in the channel direction, it will be more efficient to further perform a Fourier transform in the depth (time) direction and perform a beam forming process in a two-dimensional frequency space (which may be referred to as a "k-space"). Thus, in a third embodiment, an example will be explained in which a Fourier transform in the channel direction is performed, and subsequently, a Fourier transform in the depth (time) direction is further performed to perform a beam forming process.

An overall configuration of the ultrasound diagnosis apparatus 1 according to the third embodiment is almost the same as the overall configuration of the ultrasound diagnosis apparatus 1 according to the first embodiment illustrated in FIG. 1, except that the configuration of a part of the Doppler processing circuitry is different. Thus, the following explanations will focus on the configuration of the Doppler processing circuitry according to the third embodiment.

Figure 19:
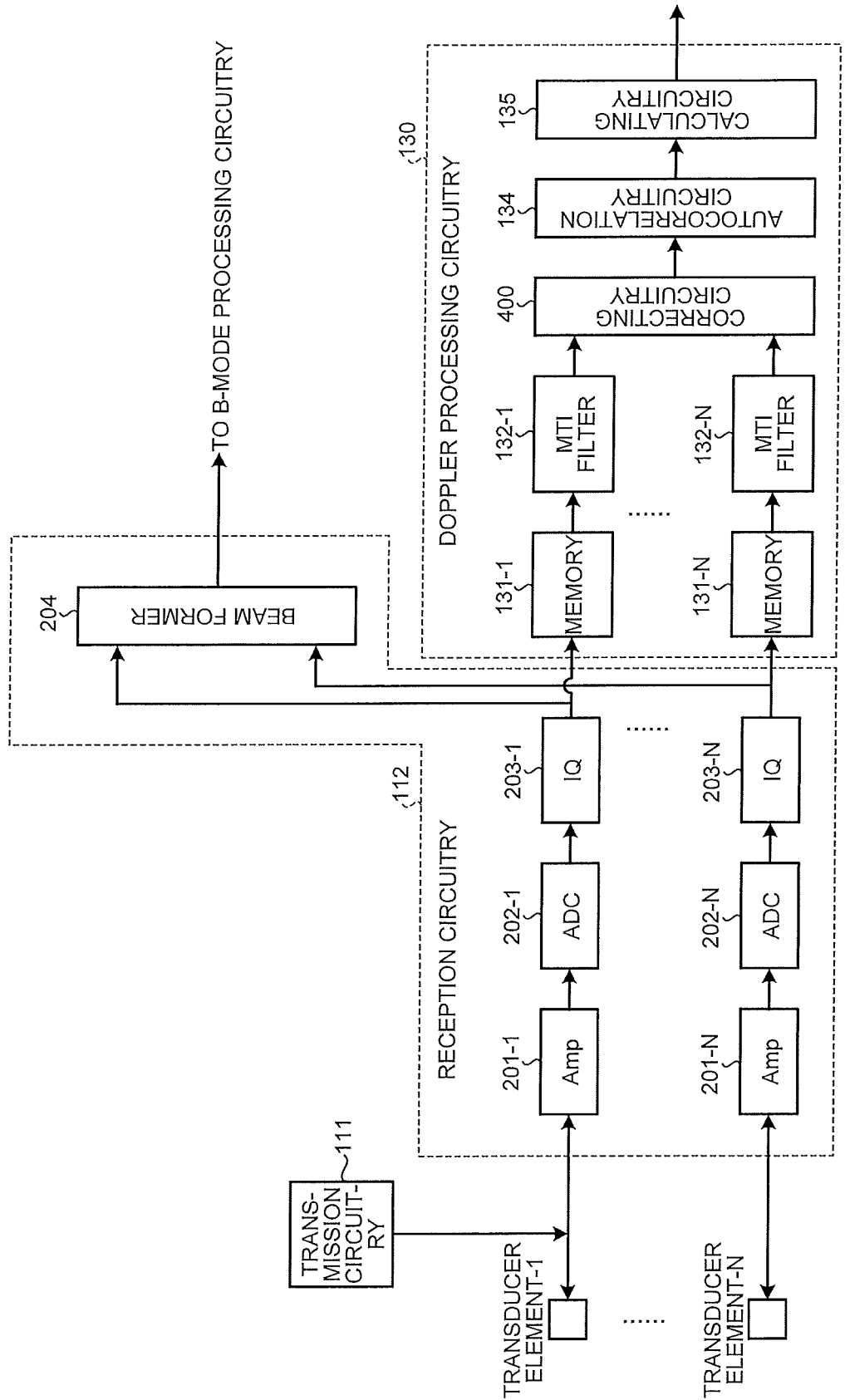
FIG. 19 is a block diagram illustrating exemplary configurations of reception circuitry and Doppler processing circuitry according to a third embodiment.

FIG. 19 is a block diagram illustrating exemplary configurations of the reception circuitry 112 and the Doppler processing circuitry 130 according to the third embodiment. Because the configuration of the reception circuitry 112 illustrated in FIG. 19 is the same as the configuration of the reception circuitry 112 illustrated in FIG. 5, detailed explanations thereof will be omitted. Further, with reference to FIG. 19, an example will be explained in which a blood flow image is displayed by implementing the ultrahigh-speed framerate method realized by applying the all-raster parallel simultaneous reception to the high framerate method.

Similarly to the Doppler processing circuitry 130 illustrated in FIG. 5, as the sub circuits to perform processes on the reflected-wave signal received by the transducer element-1, the Doppler processing circuitry 130 includes the memory 131-1 and the MTI filter 132-1. Further, as the sub circuits to perform processes on the reflected-wave signal received by the transducer element-N, the Doppler processing circuitry 130 includes the memory 131-N and the MTI filter 132-N. When it is not necessary to distinguish the memory 131-1 and the memory 131-N from each other, these memories will be referred to as the memories 131. When it is not necessary to distinguish the MTI filter 132-1 and the MTI filter 132-N from each other, these MTI filters will be referred to as the MTI filters 132.

Correcting circuitry 400 is configured to perform a correcting process to suppress side lobes caused by highly-reflective members. In other words, the correcting circuitry 400 according to the third embodiment is configured to generate a first conversion signal by performing a Fourier transform in the channel direction on the first blood flow signals and to suppress a component in a predetermined direction in the first conversion signal. In this situation, as the component in the predetermined direction, the correcting circuitry 400 extracts, from the first conversion signal, such a component of which the slope with respect to the channel direction forms a straight line within a predetermined range and further suppresses the extracted component in the first conversion signal.

Subsequently, after suppressing the component in the predetermined direction in the first conversion signal, the correcting circuitry 400 according to the third embodiment generates a second conversion signal by further performing a Fourier transform in the depth direction. In this situation, in a k-space obtained by performing the two-dimensional Fourier transform on the first blood flow signals, the axis resulting from the Fourier transform in the channel direction will be referred to as a kx axis, whereas the axis resulting from the Fourier transform in the time direction will be referred to as a kt axis. Because a k-space of an echo distribution has a kx axis and a kz axis, it is necessary to perform a coordinate transformation from the kx-kt coordinate system to the kx-kz coordinate system. For this reason, the correcting circuitry 400 according to the third embodiment performs the coordinate transformation on the second conversion signal in the two-dimensional frequency space.

Further, after performing the coordinate transformation on the second conversion signal in the two-dimensional frequency space, the correcting circuitry 400 according to the third embodiment generates a second blood flow signal by performing an inverse Fourier transform in the channel direction and the depth direction. In other words, the correcting circuitry 400 obtains a signal on which a beam forming process has been performed, by performing the coordinate transformation on the second conversion signal and subsequently performing the two-dimensional inverse Fourier Transform (a 2D-IFFT).

Further, the autocorrelation circuitry 134 is configured to perform the autocorrelation calculation by using the reflected-wave data generated by the beam former 133. The calculating circuitry 135 is configured to estimate velocity (V), power (P), and dispersion (T) values of the blood flow signal.

Figure 20:
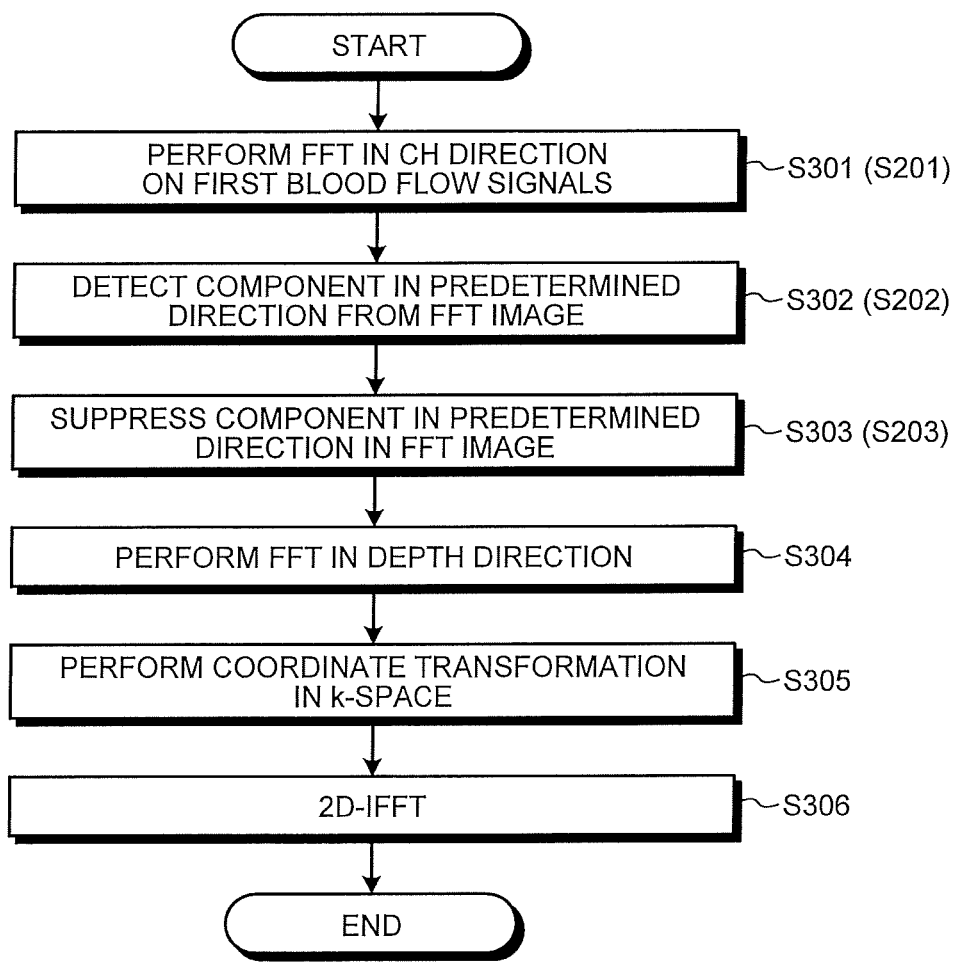
FIG. 20 is a flowchart illustrating a procedure in a second blood flow signal extracting process performed by the Doppler processing circuitry according to the third embodiment.

Next, a procedure in a process performed by an ultrasound diagnosis apparatus according to the third embodiment will be explained. The procedure in the process performed by the ultrasound diagnosis apparatus according to the third embodiment is almost the same as the procedure in the process illustrated in FIG. 14, except for the difference from the second blood flow signal extracting process at step S5 in FIG. 14. For this reason, the following explanations fill focus on the second blood flow signal extracting process according to the third embodiment. FIG. 20 is a flowchart illustrating a procedure in the second blood flow signal extracting process performed by Doppler processing circuitry according to the third embodiment. The processes in FIG. 20 correspond to the process at step S5 in FIG. 14.

Steps S301 through S306 in FIG. 20 are steps realized by the correcting circuitry 400. The processes at steps S301 through S303 in FIG. 20 are the same as the processes at steps S201 through S203 in FIG. 18.

At step S304, the correcting circuitry 400 performs an FFT in the depth direction on the first conversion signal in which the component in the predetermined direction has been suppressed. As a result, the correcting circuitry 400 obtains the second conversion signal. After that, at step S305, the correcting circuitry 400 performs the coordinate transformation in the k-space on the second conversion signal. Subsequently, after performing the coordinate transformation on the second conversion signal, at step S306, the correcting circuitry 400 performs the 2D-IFFT. In this situation, prior to the process at step S301, the correcting circuitry 300 may further perform the suppressing process at step S102 illustrated in FIG. 15.

As explained above, in the third embodiment, the Fourier transform in the channel direction is performed on the first blood flow signals, and the Fourier transform in the depth (time) direction is further performed to perform the beam forming process in the two-dimensional frequency space. The beam forming process realized with the two-dimensional Fourier transform has the smallest calculation amount when either a plane wave or a diffuse wave is transmitted. As a result, according to the third embodiment, it is possible to make the beam forming process more efficient.

Other Embodiments

Possible embodiments are not limited to the embodiments described above.

Figure 21:
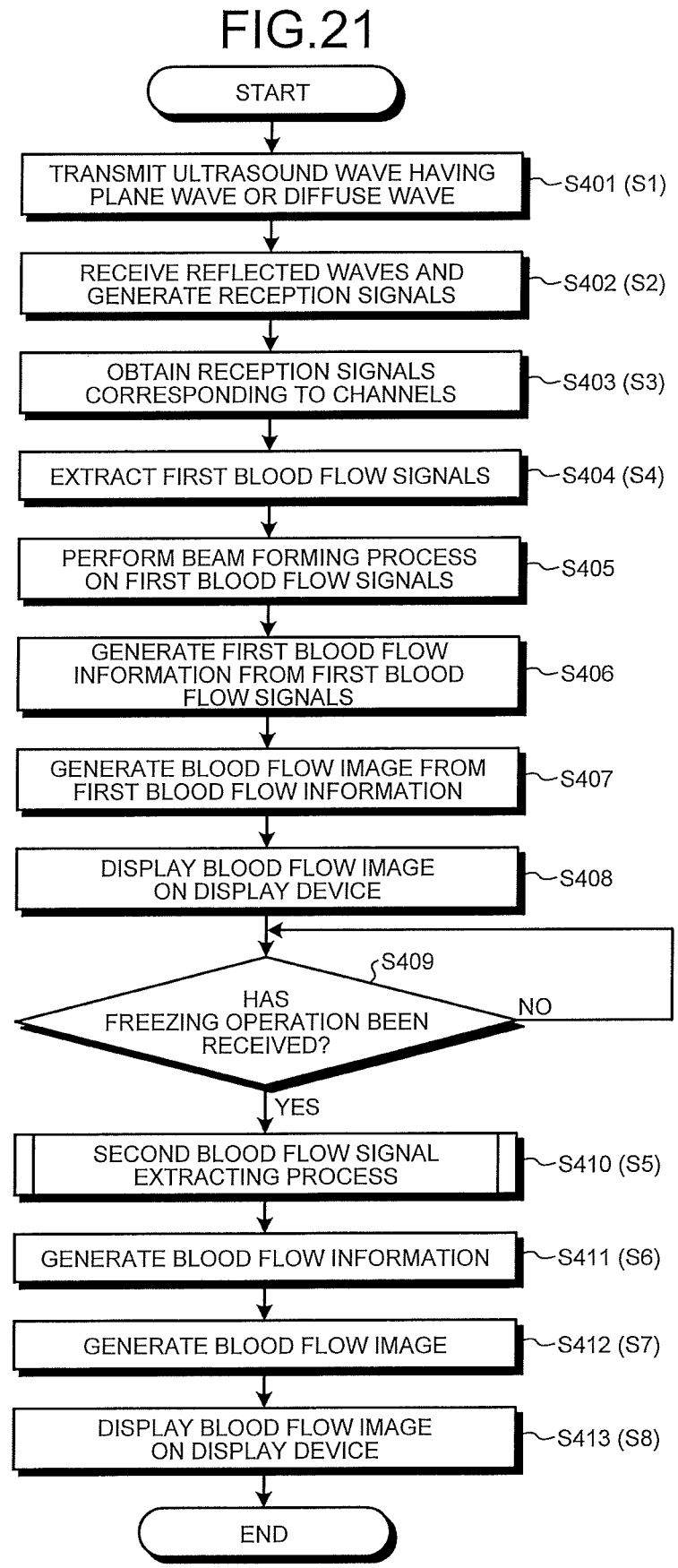
FIG. 21 is a flowchart illustrating a procedure in a process performed by an ultrasound diagnosis apparatus according to another embodiment.

In the embodiments described above, the example is explained in which the correcting process is performed during the ultrasound scan; however, possible embodiments are not limited to this example. For instance, in the Doppler processing circuitry 130, the correcting circuitry 300 and the beam former 133 may be configured to generate the blood flow information by performing the beam forming process on the first blood flow signals while an ultrasound wave is being transmitted and received and to generate the blood flow information from the second blood flow signal on which the beam forming process has been performed, after a freezing operation. With reference to FIG. 21, a procedure in a process performed by an ultrasound diagnosis apparatus according to another embodiment will be explained.

FIG. 21 is a flowchart illustrating the procedure in the process performed by the ultrasound diagnosis apparatus according to said another embodiment. The processes at steps S401 through S404 in FIG. 21 correspond to the processes at steps S1 through S4 in FIG. 14. With reference to FIG. 21, an example will be explained in which a blood flow image is displayed by implementing the ultrahigh-speed framerate method realized by applying the all-raster parallel simultaneous reception to the high framerate method.

Step S405 is a step realized by the beam former 133. At step S405, the beam former 133 performs the beam forming process on the first blood flow signals. In that situation, the correcting circuitry 300 forwards the first blood flow signals received from the MTI filters 132 to the beam former 133.

Step S406 is a step realized by the calculating circuitry 135. At step S406, the calculating circuitry 135 calculates the blood flow information from the first blood flow signals resulting from the beam forming process. For example, as the blood flow information, the calculating circuitry 135 estimates velocity (V), power (P), and dispersion (T) values of the blood flow signals.

Step S407 is a step realized by the image generating circuitry 140. At step S407, the image generating circuitry 140 generates a blood flow image from the blood flow information. Steps S408 and S409 are steps realized by the processing circuitry 170. At step S408, the processing circuitry 170 causes the display 13 to display the blood flow image. In that situation, because the correcting process to suppress side lobes occurring from highly-reflective members has not been performed, the blood flow image displayed on the display 13 may have the occurrence of an arc-shaped artifact.

At step S409, the processing circuitry 170 judges whether a freezing operation has been received. In this situation, when it is determined that no freezing operation has been received (step S409: No), the processing circuitry 170 repeatedly performs the judging process at step S409. On the contrary, when it is determined that a freezing operation has been received (step S409: Yes), the processing circuitry 170 causes the Doppler processing circuitry 130 to perform the second blood flow image extracting process at step S410. In this situation, the second blood flow image extracting process at step S410 is performed by using any of the processing procedures explained with reference to FIGS. 15, 18, and 20. In other words, the Doppler processing circuitry 130 stores the reception signals corresponding to the plurality of frames and to the channels into the memory and extracts the second blood flow signal by reading the stored reception signals after the freezing operation.

The processes at steps S411 through S413 in FIG. 21 are the same as the processes at steps S6 through S8 in FIG. 14. In that situation, because the correcting process is performed to suppress side lobes occurring from highly-reflective members, the display 13 displays a blood flow image in which arc-shaped artifacts have been suppressed. Further, the processing circuitry 170 may cause the display 13 to display the blood flow image in slow motion after a freezing operation.

As explained above, in said another embodiment, the blood flow image is generated without performing the process of suppressing the artifacts during the ultrasound scan. In this situation, by employing the MTI filters 132, the ultrasound diagnosis apparatus 1 extracts the first blood flow signals by applying the filter configured to suppress the signals originating from tissues to between the frames, with respect to the reception signals prior to the beam forming and further generates the blood flow image on the basis of the blood flow information generated from the first blood flow signals. Alternatively, the ultrasound diagnosis apparatus 1 may extract the first blood flow signals by applying the MTI filters 132 to the reception signals resulting from the beam forming process and further generate the blood flow signal on the basis of the blood flow information generated from the first blood flow signals. Subsequently, after freezing the ultrasound scan, the ultrasound diagnosis apparatus 1 reads the data from the memories 131, extracts the second blood flow signal by performing the process to suppress the artifacts, and further generates the blood flow image on the basis of the blood flow information generated from the second blood flow signal. After that, the ultrasound diagnosis apparatus 1 causes the display 13 to display the generated blood flow image in slow motion. As a result, when the beam forming process is performed by using software, it is also possible to significantly reduce the load of the beam forming process.

Figure 22:
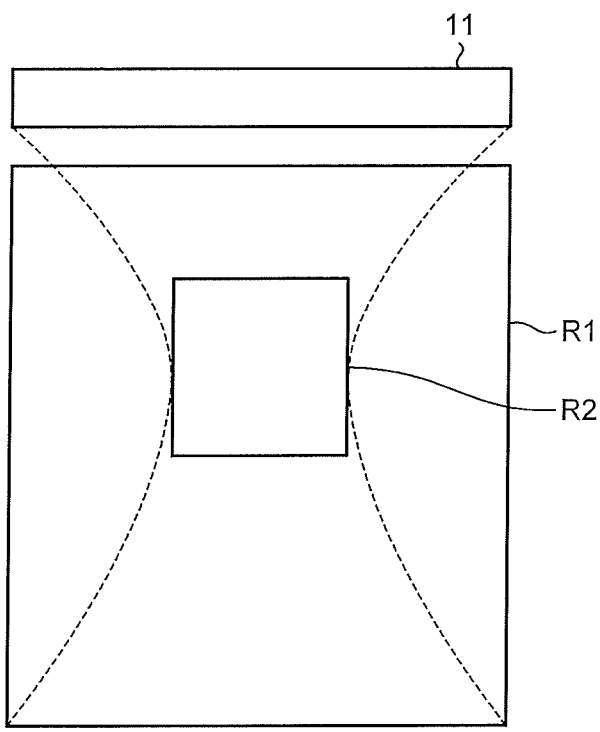
FIG. 22 is a drawing for explaining yet another embodiment.

Further, in the embodiments above, the example is explained in which the transmission circuitry 111 transmits the ultrasound wave having either a plane wave or a diffuse wave by controlling the plurality of transducer elements included in the ultrasound probe; however, possible embodiments are not limited to this example. For instance, when the region to be imaged is small, it is also acceptable to transmit an ultrasound wave while applying a transmission focus. FIG. 22 is a drawing for explaining yet another embodiment. FIG. 22 illustrates the ultrasound probe 11, a region R1 that can be imaged when all the transducer elements of the ultrasound probe 11 are used, and a region R2 that is actually subject to the imaging process. In this situation, for example, when the region R2 that is actually subject to the imaging process is smaller than the region R1 that can be imaged when the imaging process is performed by using all the transducer elements of the ultrasound probe 11, the transmission circuitry 111 may apply a transmission focus as indicated by the broken line in FIG. 22. In other words, the transmission circuitry 111 causes the ultrasound wave to be transmitted by applying the transmission focus, while controlling a plurality of transducer elements included in the ultrasound probe.

Further, in the embodiments described above, the example is explained in which the blood flow image is displayed by implementing the ultrahigh-speed framerate method realized by applying the all-raster parallel simultaneous reception to the high framerate method; however, possible embodiments are not limited to this example. For instance, the embodiments described above are applicable to situations where the all-raster parallel simultaneous reception is used, without using the high framerate method.

Further, the processes performed by the ultrasound diagnosis apparatus in any of the embodiments described above may be performed by an apparatus other than the ultrasound diagnosis apparatus. For example, the signal corresponding to the channels prior to the beam forming process are stored into the storage circuitry 160 via a bus from the reception circuitry 112. Further, the apparatus other than the ultrasound diagnosis apparatus may be configured, for example, to read the signal corresponding to the channels prior to the beam forming process after the ultrasound scan is stopped, to calculate the blood flow information by extracting the second blood flow signal by using any of the methods described above in the first to the third embodiments, to generate the blood flow image from the blood flow information, and to cause the display 13 to display the generated blood flow image.

For example, the image processing apparatus includes an obtaining unit, an extracting unit, a calculating unit, and a controlling unit. The obtaining unit is configured to obtain reception signals that correspond to a plurality of channels and were generated from reflected waves arranged to be received mutually at the same time by a plurality of transducer elements that transmitted an ultrasound wave, by controlling the plurality of transducer elements included in an ultrasound probe. In this situation, for example, the obtaining unit is configured to cause the ultrasound wave having either a plane wave or a diffuse wave to be transmitted by controlling the plurality of transducer elements included in the ultrasound probe configured to transmit ultrasound waves and to receive reflected waves and is further configured to obtain the reception signals that correspond to the plurality of channels and were generated from the reflected waves arranged to be received mutually at the same time by the plurality of transducer elements that transmitted the ultrasound wave. Alternatively, by controlling the plurality of transducer elements included in the ultrasound probe configured to transmit ultrasound waves and to receive reflected waves, the obtaining unit may be configured to cause the ultrasound wave to be transmitted while a transmission focus is applied, and to further obtain the reception signals that correspond to the plurality of channels and were generated from the reflected waves arranged to be received mutually at the same time by the plurality of transducer elements that transmitted the ultrasound wave. The extracting unit is configured to extract, prior to a beam forming process, the first blood flow signals corresponding to the plurality of channels from the reception signals corresponding to the channels while suppressing signals originating from tissues and to further extract the second blood flow signal by performing the beam forming process after suppressing, of the extracted first blood flow signals corresponding to the plurality of channels, the component in the predetermined direction. The calculating unit is configured to calculate blood flow information from the second blood flow signal. The controlling unit is configured to generate a blood flow image from the blood flow information and to cause a display to display the generated blood flow image. In another example, the image processing apparatus includes an obtaining unit, an extracting unit, a calculating unit, and a controlling unit. The obtaining unit is configured to obtain reception signals that correspond to a plurality of channels and were generated from reflected waves arranged to be received mutually at the same time by a plurality of transducer elements that transmitted an ultrasound wave, by controlling the plurality of transducer elements included in an ultrasound probe. In this situation, for example, the obtaining unit is configured to cause the ultrasound wave having either a plane wave or a diffuse wave to be transmitted by controlling the plurality of transducer elements included in the ultrasound probe configured to transmit ultrasound waves and to receive reflected waves and is further configured to obtain the reception signals that correspond to the plurality of channels and were generated from the reflected waves arranged to be received mutually at the same time by the plurality of transducer elements that transmitted the ultrasound wave. Alternatively, by controlling the plurality of transducer elements included in the ultrasound probe configured to transmit ultrasound waves and to receive reflected waves, the obtaining unit may be configured to cause the ultrasound wave to be transmitted while a transmission focus is applied, and to further obtain the reception signals that correspond to the plurality of channels and were generated from the reflected waves arranged to be received mutually at the same time by the plurality of transducer elements that transmitted the ultrasound wave. The extracting unit is configured to extract, prior to a beam forming process, the first blood flow signals corresponding to the plurality of channels from the reception signals corresponding to the channels while suppressing signals originating from tissues and to further extract the second blood flow signal by performing the beam forming process after suppressing, of the extracted first blood flow signals corresponding to the plurality of channels, one or more signals having an amplitude equal to or larger than a predetermined threshold value. The calculating unit is configured to calculate blood flow information from the second blood flow signal. The controlling unit is configured to generate a blood flow image from the blood flow information and to cause a display to display the generated blood flow image.

In the description of the embodiments above, the constituent elements of the apparatuses illustrated in the drawings are based on functional concepts. Thus, it is not necessary to physically configure the constituent elements as indicated in the drawings. In other words, the specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a program that is analyzed and executed by the CPU or may be realized as hardware using wired logic.

Further, the image processing method explained in any of the above embodiments above may be realized by causing a computer such as a personal computer or a workstation to execute a control program that is prepared in advance. The control program may be distributed via a network such as the Internet. Further, the control program may be recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like, so as to be executed as being read by the computer from the recording medium.

According to at least one aspect of the embodiments described above, it is possible to obtain a blood flow image in which artifacts have been reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
   transmission and reception circuitry configured to generate reception signals corresponding to a plurality of channels, from reflected waves arranged to be received at a mutually same time by a plurality of transducer elements that transmitted an ultrasound wave, by controlling multiple transducer elements included in an ultrasound probe;
   extracting circuitry configured to extract, prior to a beam forming process, first signals corresponding to the plurality of channels from the reception signals corresponding to the channels while suppressing signals originating from a tissue and to further extract a second signal by performing the beam forming process after suppressing, of the extracted first signals corresponding to the plurality of channels, a component in a predetermined direction;
   calculating circuitry configured to calculate blood flow information from the second signal; and
   controlling circuitry configured to generate a blood flow image from the blood flow information and to cause a display to display the generated blood flow image.

2. An ultrasound diagnosis apparatus comprising:
   transmission and reception circuitry configured to generate reception signals corresponding to a plurality of channels, from reflected waves arranged to be received at a mutually same time by a plurality of transducer elements that transmitted an ultrasound wave, by controlling multiple transducer elements included in an ultrasound probe;

extracting circuitry configured to extract, prior to a beam forming process, first signals corresponding to the plurality of channels from the reception signals corresponding to the channels while suppressing signals originating from a tissue and to further extract a second signal by performing the beam forming process after suppressing, of the extracted first signals corresponding to the plurality of channels, one or more signals each having an amplitude equal to or larger than a predetermined threshold value;

calculating circuitry configured to calculate blood flow information from the second signal; and controlling circuitry configured to generate a blood flow image from the blood flow information and to cause a display to display the generated blood flow image.

3. The ultrasound diagnosis apparatus according to claim 1, wherein the extracting circuitry extracts the second signal by suppressing, of the first signals corresponding to the plurality of channels, one or more signals each having an amplitude equal to or larger than a predetermined threshold value and subsequently performing the beam forming process after suppressing the component in the predetermined direction.

4. The ultrasound diagnosis apparatus according to claim 1, wherein, as the component in the predetermined direction, the extracting circuitry extracts such a component of which a slope with respect to a channel direction forms a straight line within a predetermined range and further suppresses the extracted component in the first signals.

5. The ultrasound diagnosis apparatus according to claim 1, wherein the extracting circuitry generates a first conversion signal by performing a Fourier transform in a channel direction on the first signals and further extracts the second signal by performing the beam forming process after suppressing, of the first conversion signal, a component in a predetermined direction and subsequently performing an inverse Fourier transform thereon.

6. The ultrasound diagnosis apparatus according to claim 1, wherein the extracting circuitry generates a first conversion signal by performing a Fourier transform in a channel direction on the first signals, generates a second conversion signal by suppressing a component in a predetermined direction in the first conversion signal and subsequently further performing a Fourier transform in a depth direction thereon, and generates the second signal by performing a coordinate transformation on the second conversion signal in a two-dimensional frequency space and subsequently performing an inverse Fourier transform thereon in the channel direction and the depth direction.

7. The ultrasound diagnosis apparatus according to claim 5, wherein, as the component in the predetermined direction, the extracting circuitry extracts such a component of which a slope with respect to the channel direction forms a straight line within a predetermined range, from the first conversion signal, and suppresses the extracted component in the first conversion signal.

8. The ultrasound diagnosis apparatus according to claim 6, wherein, as the component in the predetermined direction, the extracting circuitry extracts such a component of which a slope with respect to the channel direction forms a straight line within a predetermined range, from the first conversion signal, and suppresses the extracted component in the first conversion signal.

9. The ultrasound diagnosis apparatus according to claim 1, wherein
the transmission and reception circuitry generates reception signals corresponding to each frame, by scanning one frame every time the ultrasound probe is caused to transmit and receive an ultrasound wave, and
the extracting circuitry extracts the first signals by applying a filter configured to suppress the signals originating from the tissue to between frames.

10. The ultrasound diagnosis apparatus according to claim 9, wherein the extracting circuitry arranges a cycle in which the beam forming process is performed to be longer than a cycle in which each frame is scanned.

11. The ultrasound diagnosis apparatus according to claim 1, wherein the extracting circuitry stores the reception signals corresponding to a plurality of frames and to the channels into a memory and extracts the second signal by reading the stored reception signals after a freezing operation.

12. The ultrasound diagnosis apparatus according to claim 11, wherein,
while the ultrasound wave is being transmitted and received, the extracting circuitry generates the blood flow information by performing the beam forming process on the first signals, and
after the freezing operation, the extracting circuitry generates the blood flow information from the second signal resulting from the beam forming process.

13. The ultrasound diagnosis apparatus according to claim 11, wherein the controlling circuitry causes the display to display the blood flow image in slow motion after the freezing operation.

14. The ultrasound diagnosis apparatus according to claim 12, wherein the controlling circuitry causes the display to display the blood flow image in slow motion after the freezing operation.

15. The ultrasound diagnosis apparatus according to claim 1, wherein, while the ultrasound wave is being transmitted and received, the controlling circuitry causes the display to display a blood flow image corresponding to one heartbeat over a time period calculated by multiplying a time period required by one heartbeat by a predetermined coefficient.

16. The ultrasound diagnosis apparatus according to claim 1, wherein the controlling circuitry identifies a two-dimensional vector indicating a flow of blood by tracking a movement of a speckle between blood flow images and causes the display to display the identified two-dimensional vector.

17. The ultrasound diagnosis apparatus according to claim 1, wherein the transmission and reception circuit causes the ultrasound wave having either a plane wave or a diffuse wave to be transmitted by controlling the multiple transducer elements included in the ultrasound probe and generates the reception signals corresponding to the plurality of channels from the reflected waves arranged to be received mutually at the same time by the plurality of transducer elements that transmitted the ultrasound wave.

18. The ultrasound diagnosis apparatus according to claim 2, wherein the transmission and reception circuit causes the ultrasound wave having either a plane wave or a diffuse wave to be transmitted by controlling the multiple transducer elements included in the ultrasound probe and generates the reception signals corresponding to the plurality of channels from the reflected waves arranged to be received mutually at the same time by the plurality of transducer elements that transmitted the ultrasound wave.

19. An image processing apparatus comprising:
obtaining circuitry configured to obtain reception signals corresponding to a plurality of channels and being generated from reflected waves arranged to be received at a mutually same time by a plurality of transducer elements that transmitted an ultrasound wave, by controlling multiple transducer elements included in an ultrasound probe;
extracting circuitry configured to extract, prior to a beam forming process, first signals corresponding to the plurality of channels from the reception signals corresponding to the channels while suppressing signals originating from a tissue and to further extract a second signal by performing the beam forming process after suppressing, of the extracted first signals corresponding to the plurality of channels, a component in a predetermined direction;
calculating circuitry configured to calculate blood flow information from the second signal; and
controlling circuitry configured to generate a blood flow image from the blood flow information and to cause a display to display the generated blood flow image.

20. An image processing apparatus comprising:
obtaining circuitry configured to obtain reception signals corresponding to a plurality of channels and being generated from reflected waves arranged to be received at a mutually same time by a plurality of transducer elements that transmitted an ultrasound wave, by controlling multiple transducer elements included in an ultrasound probe;
extracting circuitry configured to extract, prior to a beam forming process, first signals corresponding to the plurality of channels from the reception signals corresponding to the channels while suppressing signals originating from a tissue and to further extract a second signal by performing the beam forming process after suppressing, of the extracted first signals corresponding to the plurality of channels, one or more signals each having an amplitude equal to or larger than a predetermined threshold value;
calculating circuitry configured to calculate blood flow information from the second signal; and
controlling circuitry configured to generate a blood flow image from the blood flow information and to cause a display to display the generated blood flow image.

21. An image processing method comprising:
obtaining reception signals corresponding to a plurality of channels and being generated from reflected waves arranged to be received at a mutually same time by a plurality of transducer elements that transmitted an ultrasound wave, by controlling multiple transducer elements included in an ultrasound probe;
extracting, prior to a beam forming process, first signals corresponding to the plurality of channels from the reception signals corresponding to the channels while suppressing signals originating from a tissue and further extracting a second signal by performing the beam forming process after suppressing, of the extracted first signals corresponding to the plurality of channels, a component in a predetermined direction;
calculating blood flow information from the second signal; and
generating a blood flow image from the blood flow information and causing a display to display the generated blood flow image.

22. An image processing method comprising:
obtaining reception signals corresponding to a plurality of channels and being generated from reflected waves arranged to be received at a mutually same time by a plurality of transducer elements that transmitted an ultrasound wave, by controlling multiple transducer elements included in an ultrasound probe;
extracting, prior to a beam forming process, first signals corresponding to the plurality of channels from the reception signals corresponding to the channels while suppressing signals originating from a tissue and further extracting a second signal by performing the beam forming process after suppressing, of the extracted first signals corresponding to the plurality of channels, one or more signals each having an amplitude equal to or larger than a predetermined threshold value;
calculating blood flow information from the second signal; and
generating a blood flow image from the blood flow information and causing a display to display the generated blood flow image.

* * * * *